US006620937B2

(12) United States Patent
Curran et al.

(10) Patent No.: US 6,620,937 B2
(45) Date of Patent: Sep. 16, 2003

(54) INTERMEDIATES IN THE SYNTHESIS OF CAMPTOTHECIN AND RELATED COMPOUNDS AND SYNTHESIS THEREOF

(75) Inventors: Dennis P. Curran, Pittsburgh, PA (US); Hubert Josien, Hoboken, NJ (US); Sung Bo Ko, Taejon (KR)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/815,459

(22) Filed: Mar. 23, 2001

(65) Prior Publication Data

US 2001/0029298 A1 Oct. 11, 2001

Related U.S. Application Data

(60) Division of application No. 09/007,872, filed on Jan. 15, 1998, now Pat. No. 6,211,371, which is a continuation of application No. 08/436,799, filed on May 8, 1995, now abandoned, which is a continuation-in-part of application No. 08/085,190, filed on Jun. 30, 1993, now abandoned.

(51) Int. Cl.[7] .................. C07D 491/052; C07D 491/22; C07D 491/44; C07D 487/14; C07D 213/64; C07F 7/10

(52) U.S. Cl. ............................ 546/116; 546/48; 546/70; 546/300; 546/302; 546/41; 546/14; 544/342; 544/343; 544/361; 544/362

(58) Field of Search ......................... 546/116, 48, 302, 546/70; 544/342

(56) References Cited

U.S. PATENT DOCUMENTS

5,700,939 A * 12/1997 Fortunak .................... 546/116

* cited by examiner

*Primary Examiner*—Evelyn Mei Huang
(74) *Attorney, Agent, or Firm*—Bartony & Hare, LLP

(57) ABSTRACT

The present invention provides a short, convergent total synthesis of camptothecin and related compounds which consists of a novel 4+1 radical annulation. The present invention also provides novel chemical intermediates for such 4+1 radical annulations.

5 Claims, 19 Drawing Sheets

INTERMEDIATES IN THE SYNTHESIS OF CAMPTOTHECIN AND RELATED COMPOUNDS AND SYNTHESIS THEREOF

CROSS REFERENCE TO RELATED APPLICATION

This application is division of U.S. patent application Ser. No. 09/007,872, filed Jan. 15, 1998, U.S. Pat. No. 6,211,371, which is a continuation of U.S. patent application Ser. No. 08/436,799, filed May 8, 1995, abandoned, which is a continuation in part of U.S. patent application Ser. No. 08/085,190, filed Jun. 30, 1993, abandoned, the disclosures of which are incorporated herein by reference.

GOVERNMENT INTERESTS

This invention was made with government support under grant RO1 GM33372 awarded by the National Institutes of Health. The government has certain rights in this invention.

FIELD OF THE INVENTION

The present invention relates to novel intermediates in the synthesis of camptothecin and related compounds, and to methods of synthesis of camptothecin and related compounds via a 4+1 radical annulation.

BACKGROUND OF THE INVENTION

As part of an antitumor screening program, Wall and coworkers identified the novel pyrrolo [3,4-b] quinoline alkaloid (S)-camptothecin in 1966. Wall, M. E., et al., *J. Am. Chem. Soc.*, 88, 3888 (1966); Carte, B. K., et al., *Tetrahedron*, 46, 2747 (1990). The chemical formula of (S)-camptothecin is provided below.

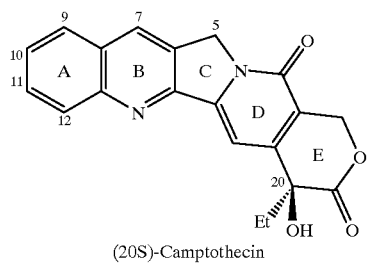

(20S)-Camptothecin

1a

This compound had been isolated from the extracts of the *camptotheca acuminata* tree. In addition to its novel structure, camptothecin has two other unusual features: its quinoline nitrogen is not very basic, and its α-hydroxy lactone is quite reactive. For a few years, camptothecin appeared to be an exciting lead compound for cancer chemotherapy. However, initial medical excitement waned because of the relative insolubility of camptothecin. Moreover, clinical trials of a water-soluble sodium salt derived by opening the lactone of camptothecin were abandoned because of unpredictable toxicity problems. The sodium salt is considerably less potent than camptothecin and its activity is now thought to result from lactonization to reform camptothecin in vivo. These observations delayed preclinical and clinical research of camptothecin and its analogs for 20 years.

However, oncological and medicinal interest in camptothecin was reborn in the mid 80s when details about the unique mechanism of action of camptothecin and its analogs began to unfold. Camptothecin acts on DNA through the intermediacy of the enzyme topoisomerase I. See Kaufman, S. H., et al., *J. Nat'l. Cancer Inst*, 85, 271 (1993); Hsiang, Y. H., et al., *J. Biol. Chem.* 260, 14873 (1985); Hsiang, Y. H. and Liu, L. F., *Cancer Res.*, 48, 1722 (1988); Liu, L. F., *Annu. Rev. Biochem.*, 58, 351 (1989); "Chemotherapy: Topoisomerases as Targets," *Lancet*, 335, 82 (1990). The topoisomerases solve topological problems of DNA. Human topoisomerase I (100 kd) catalyzes the relaxation of supercoiled DNA by cleaving a single phosphodiester bond to form a temporary phosphoryl tyrosine diester. This intermediate is called the "cleavable complex." The other end of the cleaved strand is free, and can "unwind" before the DNA chain is resealed by reverse of the original reaction. Topoisomerase I acts without cofactors, its reactions are fully reversible, and it is thought to be especially important for unwinding DNA (thermodynamically favorable) during replication. In contrast, topoisomerase II acts by cleaving and resealing (after strand passage) both strands of DNA, and its reactions are coupled with ATP hydrolysis.

There is now very strong evidence that camptothecin kills cells by binding to and stabilizing the covalent DNA-topoisomerase I complex in which one strand of DNA is broken (the cleavable complex). The progression from the ternary camptothecin/topoisomerase I/DNA complex to cell death is not well understood, and is the subject of intense investigation. Several lines of evidence (including the complete reversibility of ternary complex formation) indicate that the ternary complex does not simply tie up DNA, but itself actively initiates cell death. For this reason, camptothecin is often called a "topoisomerase poison."

Until very recently, camptothecin and its close relatives were the only known topoisomerase I poisons. In contrast, there are now many known antitumor agents that are topoisomerase II poisons. These include large classes of intercalators like the acridines and anthracyclines that were originally thought to interact only with DNA. Such topoisomerase II poisons may be inherently less selective than camptothecin because their interactions with DNA do not require topoisomerase II. Important non-intercalative topoisomerase II poisons include members of the podophyllotoxin class.

Camptothecin is being touted as an unusually important lead in cancer chemotherapy because of its selectivity. The (potential) selective toxicity of camptothecin towards cancer cells emanates from two sources: 1) camptothecin is highly selective for the DNA/topoisomerase I cleavable complex, and 2) replicating cancer cells contain elevated levels of topoisomerase I (15-fold increases over normal cells have recently been measured).

New interest resulting from the identification of camptothecin's mechanism of action has initiated (i) structure-activity relationship studies and (ii) a new series of clinical trials. Recent tests in xenografts by Potmesil and coworkers were very promising. See Giovanella, B. C., et al., *Science*, 246, 1046 (1989). Racemic 9-aminocamptothecin was found to be very effective in treating mice carrying colon cancer xenografts. Indeed most of the mice in the study were cured by 9-aminocamptothecin at dose levels that were well tolerated. The improved efficacy of 9-aminocamptothecin compared to current drugs used in colon cancer chemotherapy (like 5-fluorouracil) was dramatic. 10,11-Methylenedioxycamptothecin also showed very good promise. The significance of these results is very high. Human colon cancer is a major problem in clinical oncology, and one in twenty-five Americans will develop this disease during their lifetime.

More recently, other close relatives (analogs) of camptothecin have also emerged as excellent candidates for chemotherapy against a variety of tumor types. In an attempt to overcome the problem of low solubility encountered earlier with camptothecin, most of such compounds are designed to be water-soluble. Several of these compounds are undergoing clinical trials. See Sinha, B. K., *Drugs*, 49, 11 (1995). Pommier, Y. et al., *J. Natl. Cancer Inst.*, 86, 836 (1994). Potmesil, M. *Cancer Res.*, 54, 1431 (1994). Curran, D. P., "The Camptothecins: A Reborn Family of Antitumor Agents," *J. of the Chinese Chem. Soc.*, 40, 1–6 (1993), the disclosure of which is incorporated herein by reference. See also Sawada, S., *Chem. Pharm. Bull.*, 39, 1446 (1991); Giovanella, B. C., et al., *Science* (Washington, D.C.), 246, 1046 (1989); Kingsbury, W. D., et al.; *Med. Chem.*, 34, 98 (1991); Sawada, S., et al.; *Chem. Pharm. Bull.*, 39, 1446 (1991), Nicholas, A. W., et al. *J. Med. Chem.* 33, 972 (1991).

Such compounds, for example, include topotecan (often called TPT), currently undergoing phase III studies, and irinotecan (often called CPT-11), currently undergoing phase II studies. See Abigerges, D., et al., *J. Clin. Oncol.*, 13, 210 (1995). Potmesil, M., *Cancer Res.*, 54, 1431 (1994). Miller, A. et al., *J. Clin. Oncol.*, 12, 2743 (1994). Fukuoka, M. et al., *Canc. Chemotherap. Pharmacol.*, 34, 105 (1994). Shimada, Y. et al., *J. Clin. Oncol.*, 11, 909 (1993). Another analog, 10,11-ethylenedioxy-7-(4-methylpyrazino)-camptothecin, has been recently introduced by Glaxo and is now in clinical trials. See Eur. Pat. Appl. EP 540,099 (C1. C07D491/22), May 5, 1993, U.S. application Ser. No. 784, 275, Oct. 29, 1991. Luzzio, M. J. et al., *J. Med. Chem.*, 38, 395 (1995). See also Wall, M. E. et al., *J. Med. Chem.*, 36, 2689 (1993). The results of these recent trials suggest that these compounds hold excellent promise for the clinical treatment of a number of types of refractory solid tumors.

Moreover, recent trials using new formulations have recently opened new opportunities for camptothecin derivatives previously dismissed for their poor water solubility. In this regard, it has been discovered that (i) (S)-camptothecin itself can be formulated in 20% interlipid, and (ii) this formulation is active both intramuscularly and orally. These treatments were found far superior to previous intravenous treatments. With this formulation, non-toxic doses of camptothecin suppressed growth and induced regression of cancer in thirteen human xenograft lines, including colon, lung, breast, stomach, ovary, and malignant melanoma. Camptothecin was more effective than any other clinical drug tested. See Giovanella, B. C. et al., *Cancer Res.*, 51, 3052 (1991).

More recently liposome-incorporated camptothecin has shown, when administered intramuscularly, excellent anti-tumor activities on mice xenografted with human malignant melanoma and breast carcinoma. This mode of administration appears to hold very good promise, particularly in the treatment of human lymph node metastases. See Giovanella, B. C., *Anti-Cancer Drugs*, 6, 83 (1995).

The large variety of camptothecin derivatives or analogs synthesized and studied has allowed study of the features of the molecule which are preferable for cytotoxicity. See Kaufmann, S. H. et al., *J. Natl. Cancer Inst.*, 85, 271 (1993) and references cited therein; Uehling, D. E. et al., *J. Med. Chem.*, 38, 1106 (1995); Luzzio, M. J. et al., *J. Med. Chem.*, 38, 395 (1995); Wang, H. K. et al., *Bioorg. Med. Chem. Lett.*, 5, 77 (1995); Sawada, S. et al., *Chem. Pharm. Bull.*, 42, 2518 (1994); Terasawa, H. et al., *Heterocycles*, 38, 81 (1994); Terasawa, H. et al., *J. Med. Chem.*, 37, 3033 (1994); Wall, M. E. et al., *J. Med. Chem.*, 36, 2689 (1993).

A number of structural features identified by those studies and believed important for activity are briefly summarized below. It is believed that only the (S) enantiomer of camptothecin is responsible for its bioactivity. The (R) enantiomer is believed to be inactive. The closed lactone ring and its α-hydroxyl group in position 20 are believed to be important for bioactivity. Substitution or modification of camptothecin rings reveal that numerous and varied substitution of its "northern" and "western" regions, particularly the A- and B-rings, are compatible with the biological activity. Thus, positions 7, 9 and 10, and particularly position 7, have been widely substituted with hydrophilic and lipophilic groups such as alkyl, alkylamine, benzyl, hydroxy, amino and halo groups, to provide camptothecin derivatives retaining biological activity. These groups may be unsubstituted or substituted. Such compounds include the water-soluble topotecan and irinotecan. In general, it appears that substantially any substitution can be made at the 7, 9 and 10 positions while maintaining activity. Other tolerated modifications of the A- and B-ring are the replacement of one aromatic carbon with a nitrogen atom, such as 7- or 11-azacamptothecin which exhibited increased water-solubility while maintaining activity.

It is believed that substitutions possible at position 11 to retain biological activity may be more limited. However, such substitutions include the recently developed 10,11-ethylenedioxy-7-(4-methylpyrazinomethyl)-camptothecin of Glaxo and several new 11-fluoro camptothecin analogues recently disclosed by Sawada.

In contrast, for the C-ring, the only acceptable modifications discovered to date are those in position 5. Moreover, it is believed that biological activity will be retained only if the planarity of the molecule is conserved. Concerning the ring E, the ethyl group of camptothecin has been replaced by allyl, propargyl, and benzyl groups without significantly reducing the activity.

In addition to the interest in camptothecin and its analogs as anti-tumor agents, the interest in such compounds has recently increased to even greater levels upon the discovery that camptothecin is a potent antiretroviral agent. Preil and coworkers showed that camptothecin and analogs: 1) inhibited retroviral topoisomerase I, 2) prevented retroviral infections in healthy cells, 3) reduced and eliminated retroviral infections and infected cells, and 4) did not harm cells at useful dose levels. See Priel, E., et al., *AIDS Res. Hum. Retroviruses* 7, 65 (1991). Topoisomerase II inhibitors were ineffective. These results suggest that camptothecin may represent a new avenue of investigation for the potential treatment of AIDS.

Camptothecin was synthesized about ten times during the 1970s, although some later syntheses are modifications of earlier ones. Syntheses based on the Friedlander quinoline synthesis to construct ring B were most common. Ejima, A., et al., *J. Chem. Soc., Perkin Trans.* 1, 27 (1990); Earl, R. E. and Vollhardt, K. P. C., *J. Org. Chem.* 1984, 49, 4786; Ihara, M. et al., *J. Org. Chem.*, 48, 3150 (1983); Cai, J. C. and Hutchinson, C. R., *Chem. Heterocycl. Compd.* 25, 753 (1983); Hutchinson, C. R., *Tetrahedron* 37, 1047 (1981); Cai, J. C. and Hutchinson, C. R., *The Alkaloids: Chemistry and Pharmacology;* Brossi, A. Ed.; Academic Press: New York, Vol. 21, p. 101 (1983); Schultz, A. G., *Chem. Rev.* 73, 385 (1973). Many syntheses are racemic, but resolutions have been reported. See Wani, M. C., et al. *J. Med. Chem.*, 30, 2317 (1987). More recently, a chiral auxiliary approach to asymmetric ethylation was described. See Ejima, A., et al., *Tetrahedron Lett.*, 30, 2639 (1989).

New or improved synthetic routes to camptothecin have recently been described by a number of laboratories. See Comins, D. L.; Hong, H.; Jianhua, G. *Tetrahedron Lett.*, 35, 5331 (1994). Comins, D. L.; Hong, H.; Saha, J. K.; Gao, J. H. *J. Org. Chem.*, 59, 5120 (1994). Fang, F. G.; Xie, S. P.; Lowery, M. W. *J. Org. Chem.*, 59, 6142 (1994). Rao, A. V. R.; Yadav, J. S.; Muralikrishna, V. *Tetrahedron Lett.*, 35, 3613 (1994). Wang, S.; Coburn, C. A.; Bornmann, W. G.; Danishefsky, S. J. *J. Org. Chem.*, 58,611 (1993).

It remains very desirable, however, to develop short, practical syntheses of camptothecin and its analogs.

SUMMARY OF THE INVENTION

Accordingly, the present invention provides a short, convergent total synthesis of camptothecin and related compounds via a novel 4+1 radical annulation.

In one embodiment, the 4+1 radical annulation is followed by another cyclization to simultaneously assemble rings B and C of camptothecin and related compounds. In that regard, the present invention provides generally a method of synthesizing tetracyclic compounds having the general formula

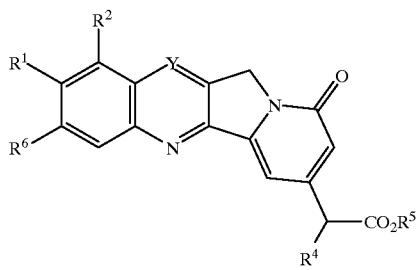

which are intermediates in many syntheses of (±)-camptothecin and related compounds. The conversion of these intermediates to (±)-camptothecin and related compounds is accomplished in two steps as known in the art: hydroxymethylation and oxidation.

The synthesis of the tetracyclic intermediates comprises the step of a 4+1 radical annulation wherein the following novel precursor:

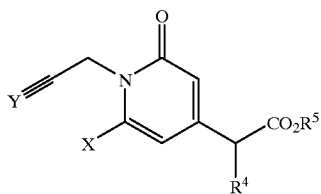

is reacted with an aryl isonitrile such as phenyl isonitrile. Y is preferably selected from the group consisting of —N and —$CR^3$. The aryl isonitrile may be unsubstituted, monosubstituted, disubstituted or trisubstituted.

$R^1$, $R^2$, $R^3$ and $R^6$ are preferably independently selected from the following groups: hydrogen, a normal alkyl group, a branched alkyl group, an allyl group, a benzyl group, an alkynyl group, a propargyl group, an alkoxyl group, a halo group, a silyl group, an amino group, a cyano group, and an acyl group. $R^6$ is more preferably selected from an alkoxyl group or a halo group. Moreover, the groups set forth for $R^1$, $R^2$, $R^3$ and $R^6$ may be substituted with a wide variety of substituents to synthesize camptothecin analogs retaining activity.

For example, normal (unbranched) and branched alkyl groups, which preferably range between $C_1$ and $C_{15}$ (and more preferably between $C_1$ and $C_{10}$), may preferably be substituted with a group or groups including, but not limited to, a benzyl group, a phenyl group, an alkoxyl group, a hydroxy group, an amino group (including, for example, free amino groups, alkyl amino groups and aryl amino groups) and an acyloxy group. Alkynyl groups (—C≡C—R) may preferably be substituted with a group or groups including, but not limited to, an alkoxyalkyl group, an amino alkyl group and a benzyl group. Acyl groups (RCO—) may preferably be substituted with a group of groups including, but not limited to, a branched or unbranched allyl group (preferably between $C_1$ and $C_{15}$; more preferably between $C_1$ and $C_{10}$), a haloalkyl group (for example, a perfluoroalkyl group), an alkoxyl group, an amino group an a hydroxy group. Alkoxyl groups (—OR) preferably comprise a branched or unbranched alkyl group (preferably between $C_1$ and $C_{15}$; more preferably between $C_1$ and $C_{10}$). Amino groups (—$NR^aR^bR^c$) may preferably be substituted with a group or groups including, but not limited to, hydrogen, an acyl group, a branched or unbranched alkyl group (preferably between $C_1$ and $C_{15}$; more preferably between $C_1$ and $C_{10}$) an alkoxyl group and an aryl group (preferably a phenyl or napthyl group). Silyl groups may preferably be substituted with a group or groups including, but not limited to, a branched or unbranched alkyl group (preferably between $C_1$ and $C_{15}$; more preferably between $C_1$ and $C_{10}$) and an aryl group (preferably a phenyl or napthyl group; more preferably a phenyl group).

In general, $R^1$, $R^2$, $R^3$ and $R^6$ are preferably not excessively bulky to maintain activity of the resultant camptothecin analog. Preferably, therefore, $R^1$, $R^2$, $R^3$ and $R^6$ independently have a molecular weight less than approximately 250. More preferably $R^1$, $R^2$, $R^3$ and $R^6$ independently have a molecular weight less than approximately 200.

$R^4$ is preferably selected from a primary or secondary alkyl group (preferably between $C_1$ and $C_{15}$; more preferably between $C_1$ and $C_{10}$), an allyl group, a propargyl group and a benzyl group. More preferably, $R^4$ is an ethyl group. $R^5$ is preferably selected from a linear or branched alkyl group (preferably between $C_1$ and $C_{15}$; more preferably between $C_1$ and $C_{10}$) or a benzyl group. Most preferably, $R^5$ is selected from linear or branched alkyl groups in the range of $C_1$ to $C_6$.

The above-described synthetic scheme is very useful for large-scale production of racemic camptothecin and analogs thereof.

In another embodiment, the present invention provides a variant of the above 4+1 radical annulation/cyclization scheme in which the key E-ring lactone is preferably introduced in optically active form prior to the radical annulation/cyclization.

In that regard, the present invention provides short, convergent, and practical syntheses of optically active pentacyclic compounds having the general formula

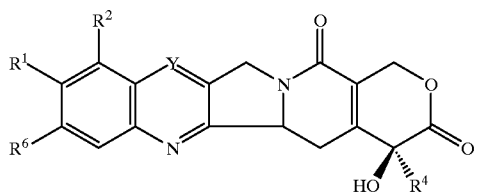

Included among these compounds, for example, are (20S)-camptothecin itself, and the related anti-tumor agents (20S)-topotecan, (20S)-irinotecan and (20S)-10,11-ethylenedioxy-camptothecin as follows.

| | | R⁶ R¹ | R² | R⁴ Y |
|---|---|---|---|---|
| Camptothecin | 1a | H H | H | Et CH |
| Topotecan | 1b | H HO | —CH₂NH(CH₃)₂ | Et CH |
| Irinotecan | 1c | H 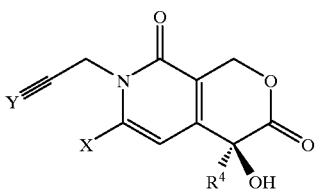 | H | Et CEt |
| 10,11-Ethylenedioxy-camptothecin | 1d | —OCH₂CH₂O— | H | Et CH |

The synthesis of the pentacyclic compounds comprises the step of a 4+1 radical annulation/cyclization wherein the following novel bicyclic precursor:

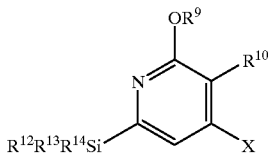

is reacted with an aryl isonitrile such as phenyl isonitrile.

In the case of a triple bond, Y is preferably selected from the group consisting of —N and —CR³. In the case of a double bond, Y is preferably —CH₂ or —CHR³. X is preferably I or Br. The aryl isonitrile may be unsubstituted, monosubstituted, disubstituted or trisubstituted.

$R^1$, $R^2$, $R^3$ and $R^6$ are preferably selected independently from the groups described previously for the synthetic route to racemic camptothecin and analogs thereof. $R^4$ is preferably selected from a primary or secondary alkyl group (preferably between $C_1$ and $C_{15}$; more preferably between $C_1$ and $C_{10}$), an allyl group, a propargyl group and a benzyl group. Most preferably $R^4$ is an ethyl group.

This synthetic route is thus useful for the large scale production of (20S)-camptothecin and its analogs, including, but not limited to (20S)-topotecan and (20S)-irinotecan. The synthetic routes of the present invention allow rapid, simple and controlled substitution in the camptothecin series of compounds while maintaining activity.

The present invention also provides the following novel precursor

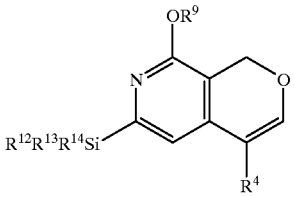

wherein $R^9$ is preferably an alkyl group (branched or unbranched and preferably between $C_1$ and $C_{15}$; more preferably between $C_1$ and $C_{10}$). $R^{10}$ is preferably selected from the group consisting of —CHO and —CH₂OCH₂CH=CHR¹¹, wherein $R^{11}$ is selected from the group consisting of an alkyl group (branched or unbranched and preferably between $C_1$ and $C_{15}$; more preferably between $C_1$ and $C_{10}$), a vinyl group, an ethynyl group and a phenyl group. $R^{12}$, $R^{13}$ and $R^{14}$ are preferably independently selected from an alkyl group (branched or unbranched and preferably between $C_1$ and $C_{15}$; more preferably between $C_1$ and $C_{10}$) and an aryl group (preferably a phenyl group or a napthyl group; more preferably a phenyl group). X is preferably selected from the group consisting of I and Br.

Still further, the present invention provides the following novel precursor wherein $R^4$, $R^9$, $R^{12}$, $R^{13}$ and $R^{14}$ are preferably selected as set forth above.

DETAILED DESCRIPTION OF THE INVENTION

Model Reaction

Figure 1:
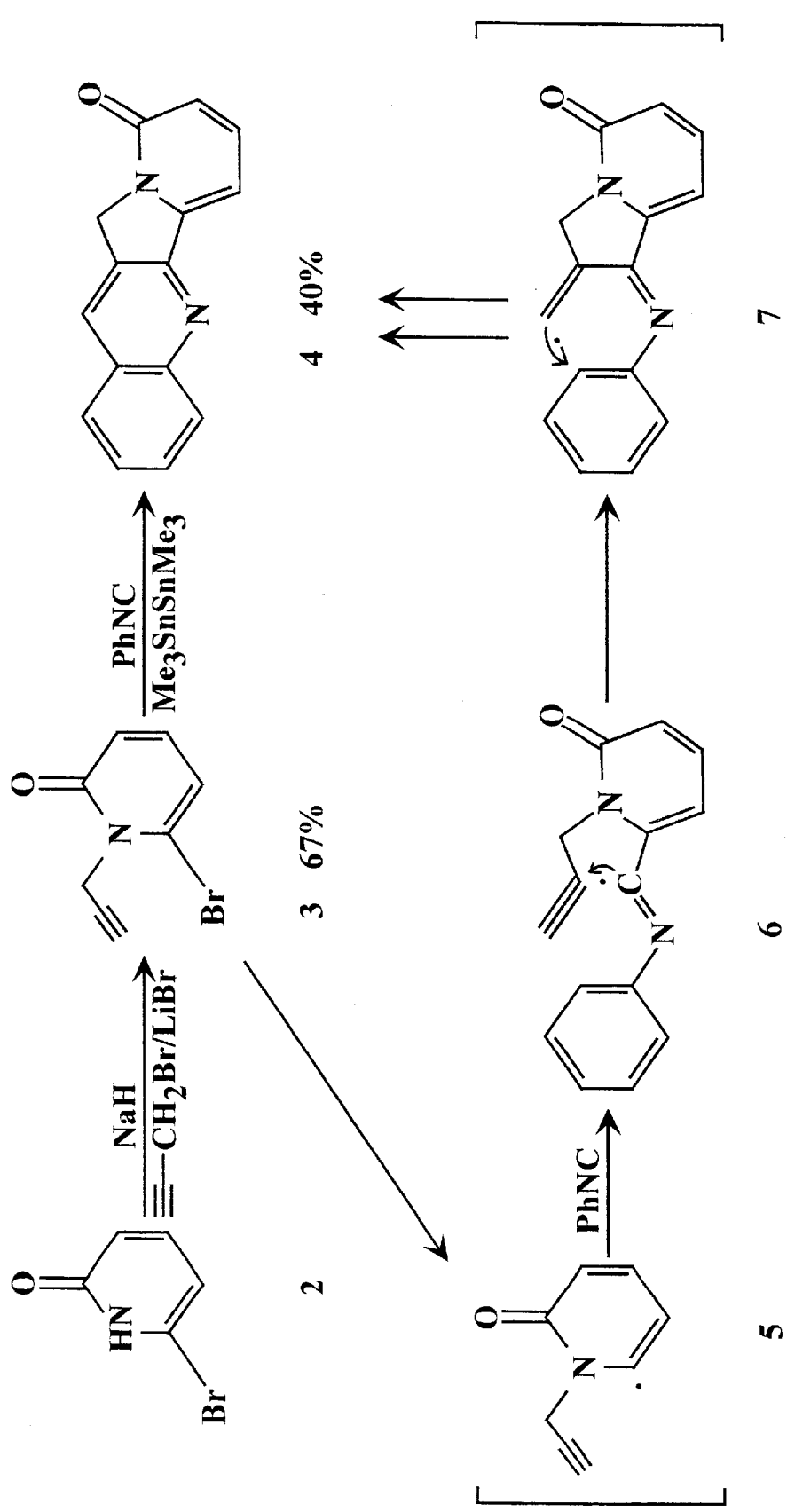
FIG. 1 is an illustration of the reaction scheme for a model 4+1 radical annulation.

The viability of the key 4+1 annulation was first demonstrated in the model reaction shown in FIG. 1.

In the reaction of FIG. 1, readily available bromopyridone 2 was N-propargylated to give 3. The synthesis of bromopyridone 2 is described in Newkome, G. R., et al, *Synthesis* 707 (1974), the disclosure of which is incorporated herein by reference. In turn, 3 reacted with phenyl isonitrile under conditions similar to those developed for reactions of simple pentynyl iodides. These conditions are detailed in Curran, D. P. and Liu, H., *J. Am. Chem. Soc.* 113, 2127 (1991), the disclosure of which is incorporated herein by reference.

Generally, an 80° C. benzene solution of 3 (preferably approximately 1 equiv), phenyl isonitrile (PhNC) (preferably approximately 5 equiv), and hexamethylditin (preferably approximately 1.5 equiv) was irradiated with a sunlamp, preferably for approximately 8 hr. After chromatography, the known tetracycle 4 was isolated in 40% yield as a white solid. Preferably, the reaction temperature is between approximately 50 and 150° C. Suitable solvents other than benzene include, but are not limited to, toluene, THF, acetonitrile and t-butanol.

FIG. 1 also shows a hypothetical mechanism for the conversion of 3 to 4. Addition of pyridone radical 5 to phenyl isonitrile to give 6 is followed by two radical cyclizations and an oxidative rearomatization. Curran, D. P. and Liu, H., *J. Am. Chem. Soc.*, 113, 2127 (1991); Leardini, R. et al., *J. Org. Chem.*, 57, 1842 (1992); Bowman, W. R. et al., *Tetrahedron*, 47, 10119 (1991), the disclosures of which are incorporated herein by reference. See also Stork, G.; Sher, M. M., *J. Am. Chem. Soc.*, 105, 6765 (1983); Barton, D. H. R.; Ozbalik, N.; Vaher, B. *Tetrahedron*, 44, 3501 (1988).

Synthesis of (±)-Camptothecin

Figure 2:
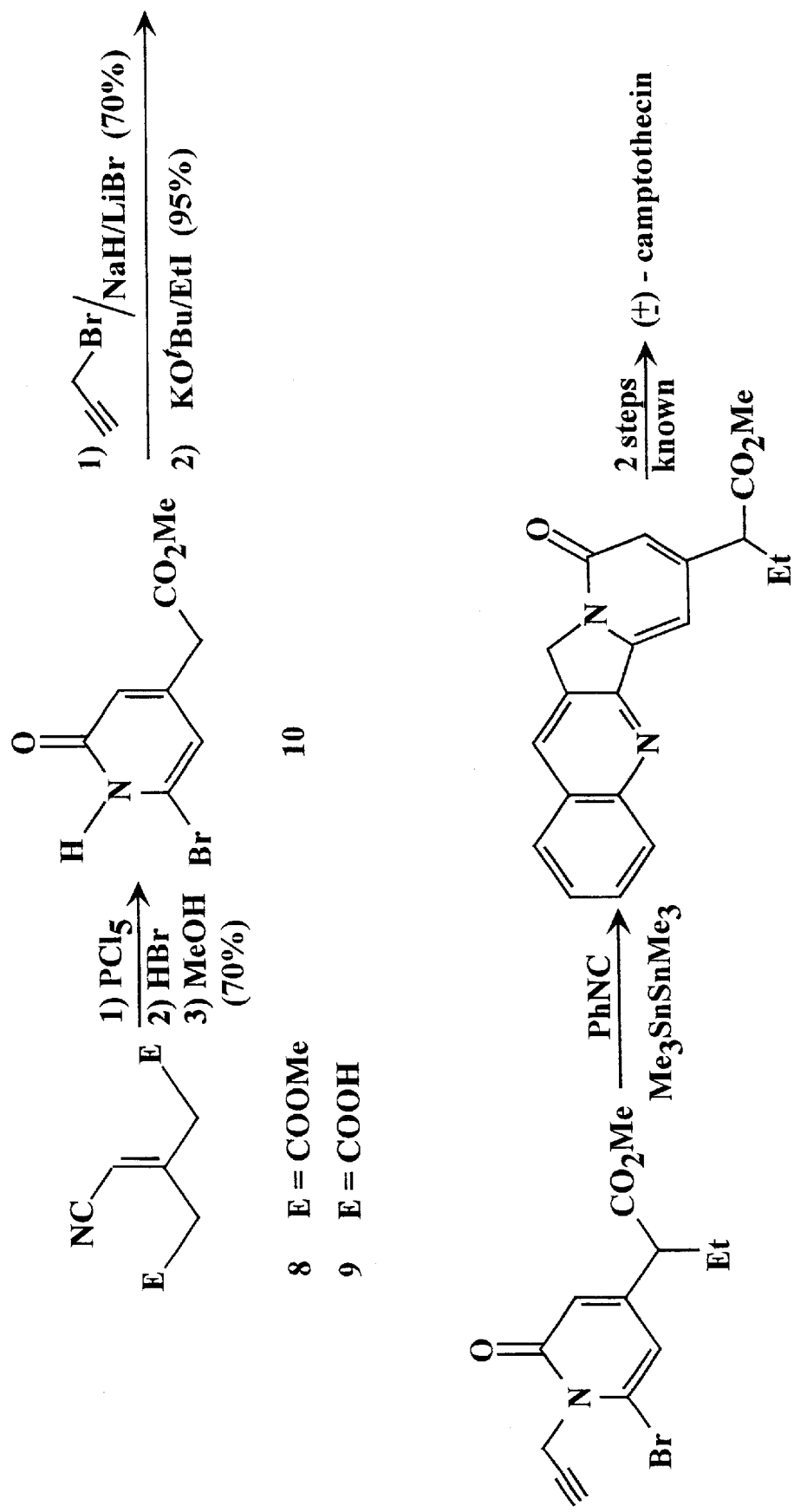
FIG. 2 is an illustration of a synthetic scheme for the synthesis of camptothecin via a 4+1 radical annulation.

The formal total synthesis of (±)-camptothecin is shown in FIG. 2. Nitrile 8 (dimethyl 3-(cyanomethylidene) pentanedioate) was first prepared by standard Doebner condensation of dimethyl acetonedicarboxylate and cyanoacetic acid (70%). See Simchen, G., *Chem. Ber.*, 103, 389 (1978). A flask equipped with a Dean-Stark water separator was charged with benzene (60 mL), dimethyl acetone-1,3-dicarboxylate (34.8 g, 0.2 mol), cyanoacetic acid (18.7 g, 0.22 mol), acetic acid (5.4 g, 0.09 mol), and ammonium acetate (3.1 g, 0.04 mol). The mixture was stirred for 5 minutes and then heated with an oil bath (oil temperature 130–135° C.) until no more water was collected. Heating time was generally 6 hours and the water layer collected was around 6 mL. After the mixture was cooled to room temperature, cold water was added. This mixture was then extracted twice with ether. The combined organic phase was washed with water, saturated sodium bicarbonate solution, and brine, and dried over sodium sulfate. After removal of solvent, the crude product was purified by vacuum distillation to give 1.5 g of dimethyl acetone-1,3-dicarboxylate, and 27.2 g of nitrile 8 (104–124° C./0.03 mm) as colorless liquid, yield 69–72%. Nitrile 8 was characterized as follows: $^1$H NMR (300 MHz, CDCl$_3$) δ5.43 (1 H , s), 3.57 (3 H, s), 3.55 (3 H, s), 3.45 (2 H, s), 3.26 (2 H, s); $^{13}$C NMR (75 MHz, CDCl$_3$) δ168.8, 168.5, 151.7, 115.2, 102.6, 52.0 (2 C), 40.5, 38.8; IR (neat) 2224, 1738 cm$^{-1}$.

Standard saponification (KOH/EtOH) gave diacid 9. Conversion of diacid 9 to bromopyridone 10 (methyl 2-(6-bromo-2(1H)-pyridon-4-yl) acetate) was accomplished by modification of a known method to prepare chloropyridones. The diacid was first treated with PCl$_5$, and then gaseous HBr (10 equiv) was introduced. See Simchen, G., *Chem. Ber.*, 103, 389 (1978).

In general, potassium hydroxide (10 g, 180 mmol) was added to a 0° C. solution of nitrile 8 (7.88 g, 40 mmol) in ethanol (160 mL) with stirring. The reaction mixture was stirred at room temperature ("RT") for 2 days. After solvent removal, ice-water (100 mL) was added. Then the mixture was immersed in an ice-water bath, and 6N HCl was added slowly until the pH value reached to 1. This solution was saturated with sodium chloride, and extracted with ethyl acetate (70 mL×4). The combined organic phase was dried over sodium sulfate. After solvent removal under reduced pressure (via rotary evaporation and vacuum pumping), 6.87 g of 3-(cyanomethylidene) pentanedioic acid 9 was collected as yellow or orange solids.

These solids were crushed to powders and methylene chloride (270 mL) was added. The mixture was cooled to 0° C. and charged with phosphorus pentachloride (17.1 g, 82 mmol) under argon. The suspension was stirred at room temperature until all the white solids dissolved (3–9 h). The flask was cooled with an acetone-dry-ice bath, evacuated with an aspirator, and sealed.

Gaseous anhydrous hydrogen bromide (about 10 L, 400 mmol) was introduced and absorbed by the solution. The vacuum was then released by filling the vessel with argon. The flask was equipped with a drying-tube which was connected to a gas trap to absorb excess HBr. The solution was stirred at −78° C. for 1 h and at room temperature for 8 h. The reaction mixture was cooled to −78° C. again. Anhydrous methanol (15.4 g, 480 mmol) was added in one portion. The solution was then slowly warmed to room temperature and stirred for 2 more hours. After addition of ice-water (150 mL), two layers were separated. The aqueous layer was extracted with methylene chloride (100 mL×2). The combined organic phase was dried over sodium sulfate. After removal of solvent, the residue was applied to chromatography (silica gel, CHCl$_3$/EtOAC) to give 6.2 g of bromopyridone 10 as off-white solids, yield 63% (from nitrile 8). The product contained 3–8% of the 6-chloro analogue as detected by GC. $^1$H NMR (300 MHz, CDCl$_3$) δ11.82 (1 H, Br), 6.81 (1 H, d, J =0.8 Hz), 6.60 (1 H, d, J=0.8 Hz), 3.73 (3 H, s), 3.53 (2 H, s); $^{13}$C NMR (75 MHz, CDCl$_3$) δ169.7, 165.1, 149.4, 132.0, 117.6, 113.5, 52.6, 40.3; IR (neat) 1728, 1647, 1592, 1451 cm$^{-1}$; MS (m/e) 247 (M), 245 (M), 188, 186, 166 (base peak); HRMS calcd for C$_8$H$_8$O$_3$BrN 244.9687, found 244.9661.

N-Propargylation (70%) and C-ethylation (95%) then gave the precursor 11 for the 4+1 annulation. For C-ethylation, see Danishefsky, S. and Etheredge, S. J., *J. Org. Chem.*, 39, 3430 (1974), the disclosure of which is incorporated herein by reference.

In general, the solution of bromopyridone 10 (12.3 g, 50 mmol) in anhydrous ethylene glycol dimethyl ether (DME, 150 mL) was cooled to 0° C. to −10° C. Sodium hydride (60% suspension in mineral oil, 2.2 g, 55 mmol) was added in several portions under argon. The mixture was warmed to room temperature and stirred until hydrogen ceased to evolve (about 20 min at room temperature). Anhydrous lithium bromide (4.8 g, 55 mmol) was added. After 20 minutes, propargyl bromide (80% in toluene, 11.9 g, 100 mmol) and DMF (3.7 g, 50 mmol) were added. The mixture was heated at 65° C. for 16 hours. After solvent removal, methylene chloride and water were added to the residue. The organic layer was separated. The aqueous layer was extracted with methylene chloride. The combined organic phase was washed with water and brine, and dried over sodium sulfate. After solvent removal with a rotary evaporator, a small amount of ether was added to the residue, and solids precipitated. The solids were filtered and rinsed with ether to give approximately 9.34 g of methyl 2-(6-bromo-N-propargyl-2(1H)-pyridon-4-yl) acetate. The filtrate was concentrated and applied to column chromatography (silica gel, hexane/ethyl acetate) to give additional 1.1 g of the product as off-white solids. Total yield was 69–73%. The product contained 3–8% of the 6-chloro analogue as detected by GC. $^1$H NMR (300 MHz, CDCl$_3$) 67 6.50 (1 H, d, J=1.6 Hz), 6.43 (1 H, d, J=1.6 Hz), 5.02 (2 H, d, J=2.4 Hz), 3.72 (3 H, s), 3.40 (2 H, s), 2.29 (1 H, t, J=2.4 Hz); $^{13}$C NMR (75 MHz, CDCl$_3$) δ169.6, 161.7, 146.7, 126.3, 118.9, 112.9, 76.9, 72.6, 52.5, 40.1, 38.2; IR (neat) 3287, 1734, 1655, 1597 cm$^{-1}$; MS (m/e) 285 (M), 283 (M, base peak), 226, 224, 204, 176, 116; HRMS calcd for $C_{11}H_{10}O_3BrN$ 282.9844, found 282.9850.

Under argon, methyl 2-(6-bromo-N-propargyl-2(1H)-pyridon-4-yl) acetate (852 mg, 3 mmol) was dissolved in DME (15 mL). The solution was cooled to −60° C., and potassium tert-butoxide (353 mg, 3.15 mmol) was added. After 5 min at −60° C., the mixture was warmed to −15° C., then cooled to ±60° C. again. Ethyl iodide (1.87 g, 12 mmol) was added. After 5 minutes at ±60° C., the reaction mixture was kept in an ice-bath, and stirred overnight (0° C. to room temperature). Solvent was removed with a rotary evaporator. Methylene chloride (30 mL) and water (30 mL) were added. The organic layer was separated. The aqueous layer was extracted with methylene chloride. The combined organic phase was washed with brine, and dried over sodium sulfate. After solvent removal, the residue was applied to column chromatography (silica gel, chloroform) to give 890 mg of precursor 11a (methyl 2-6-bromo-N-propargyl-2(1H)-pyridon-4-yl) butyrate) in 95% yield. The product contained 5–10% of the 6-chloro analogue as detected by GC. $^1$H NMR (300 MHz, CDCl$_3$) δ6.52 (1 H, d, J=1.7 Hz), 6.44 (1 H, d, J=1.7 Hz), 5.01 (2 H, d, J=2.4 H), 3.69 (3 H, s), 3.22 (1 H, t, J=7.6 Hz), 2.30 (1 H, t, J=2.4 Hz), 2.00 (1 H, m), 1.72 (1 H, m), 0.90 (3 H, t, J=7.4 Hz); $^{13}$C NMR (75 MHz, CDCl$_3$) δ172.2, 161.7, 151.4, 126.3, 117.8, 111.3, 76.8, 72.5, 52.4 (2 C), 38.2, 25.3, 11.9; IR (neat) 3264, 1732, 1663, 1509 cm$^{-1}$; MS (m/e) 313 (M, base peak), 311, 284, 282, 254, 252, 232, 204, 144; HRMS calcd for $C_{13}H_{14}O_3BrN$ 311.0157, found 311.0139.

Reaction of 11a with phenyl isonitrile as described above gave pure 12a in 45% isolated yield.

Compound 12a was first prepared by Danishefsky, and has been a key intermediate in many syntheses of camptothecin. See Volkmann, R. Danishefsky, S., Eggler, J. and Soloman, D. M., *J. Am. Chem. Soc.*, 93, 5576 (1971); Cai, J. C. and Hutchinson, C. R., *Chem. Heterocycl. Compd.*, 25, 753 (1983); Hutchinson, C. R., *Tetrahedron*, 37, 1047 (1981); Cai, J. C. and Hutchinson, C. R., *The Alkaloids: Chemistry and Pharmacology*, Brossi, A. Ed., Academic Press: New York, Vol. 21, p. 101 (1983); and Schultz, A. G., *Chem. Rev.* 73, 385 (1973), the disclosures of which are incorporated herein by reference. Conversion of 12a to (±)-camptothecin is accomplished in two steps: hydroxymethylation (35%) and oxidation (quantitative). See Cai, J. C. and Hutchinson, C. R., *Chem. Heterocycl. Compd.*, 25, 753 (1983); Hutchinson, C. R., *Tetrahedron*, 37, 1047 (1981); Cai, J. C. and Hutchinson, C. R., *The Alkaloids: Chemistry and Pharmacology*, Brossi, A. Ed., Academic Press: New York, Vol. 21, p. 101 (1983); and Schultz, A. G., *Chem. Rev.* 73, 385 (1973), the disclosures of which are incorporated herein by reference.

This synthesis of the key Danishefsky tetracycle 12a under the present method requires only six steps starting from dimethyl acetonedicarboxylate, and the overall yield is currently approximately 13%.

Figure 3:
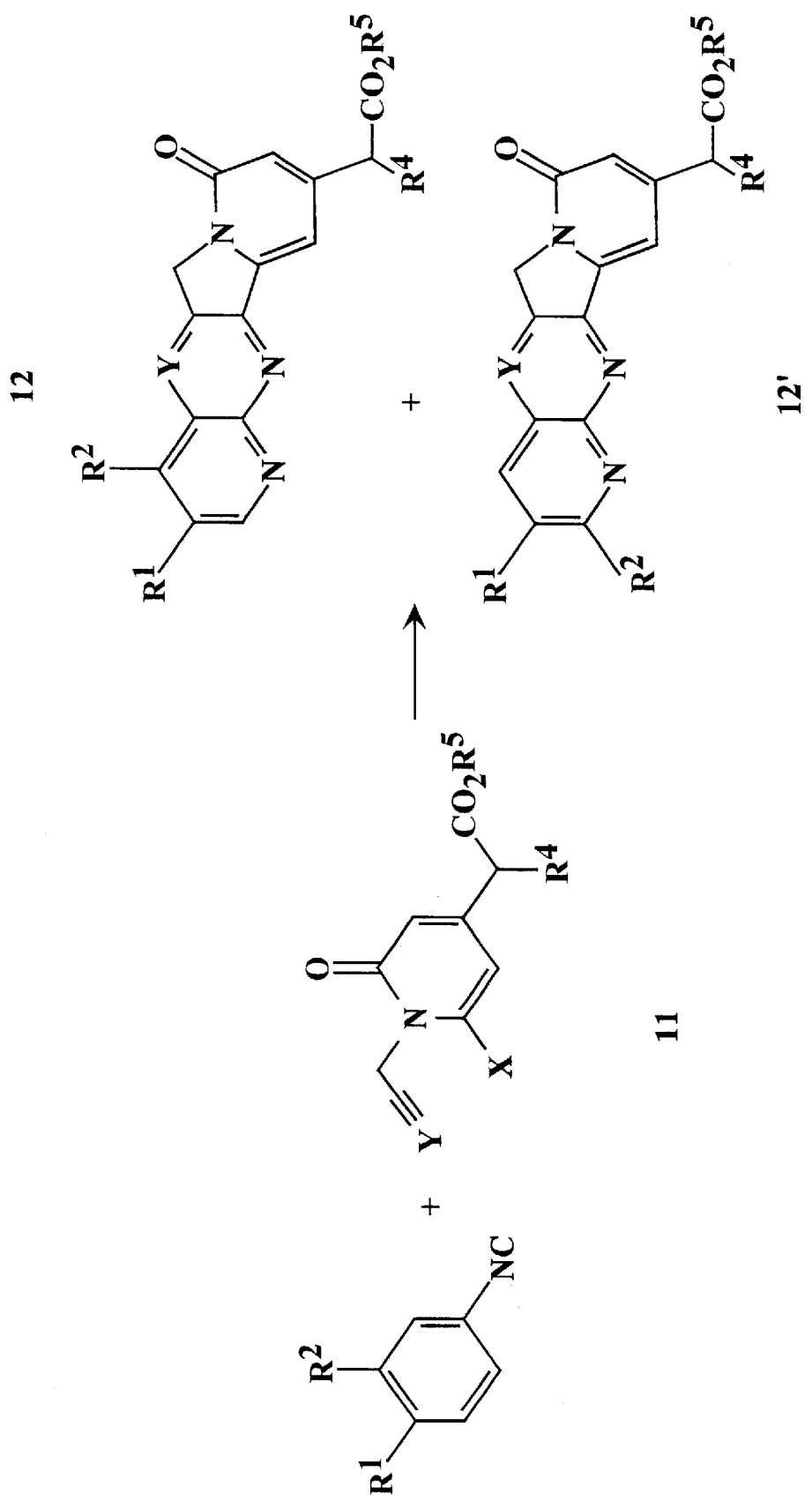
FIG. 3 is an illustration of the general synthetic scheme of the present 4+1 radical annulation.

A number of analogs of tetracycle 12a can be prepared under the present synthesis scheme. The general chemical equation for the 4+1 annulation of the present invention is given in FIG. 3. In FIG. 3, X of precursor 11 preferably is Cl, Br, or I. More preferably, X is Br or I. Y of precursor 11 may comprise N, or C—R$^3$. Regioisomers are possible when R$^2$ of tetracyclic intermediates 12 does not comprise hydrogen.

Several examples of preparation of tetracyclic intermediates via the present 4+1 annulation involving precursor 11 and an aryl isonitrile are provided below.

Preparation of Tetracyclic Intermediates

EXAMPLE 1

Figure 4B:
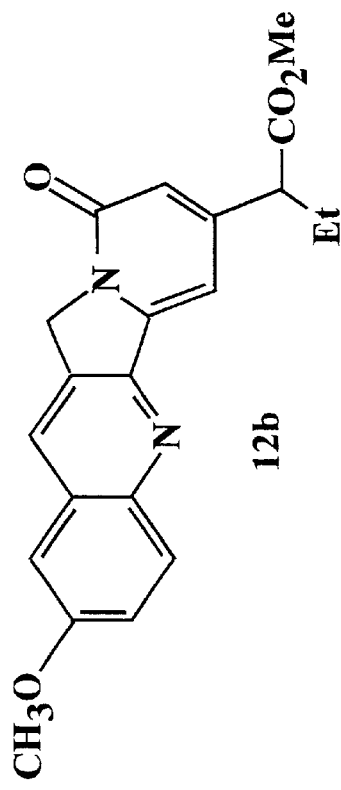
FIGS. 4a–4g provide illustrations of the chemical structures of several tetracyclic intermediates.
Figure 4D:
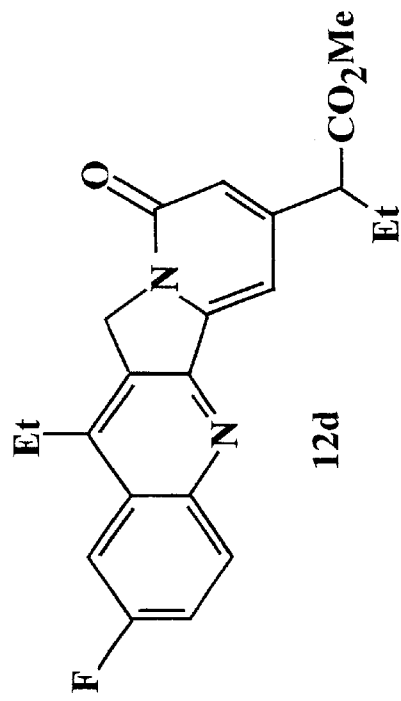
Figure 4A:
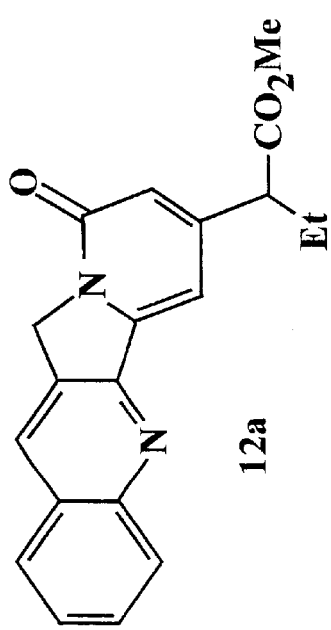

Under the general procedure, a benzene solution of precursor 11a (methyl-2-(6-bromo-N-propargyl-(1H)-pyridon-4yl)butyrate), phenyl isonitrile (1.5 to 5 equiv) and hexamethylditin (0.7 to 1.5 equiv) in a flask (flat flask preferred) was irradiated under argon with a 275W GE sunlamp or a 450W Ace Hanovia lamp for 4 to 24 hours. Solvent and isonitrile were removed under reduced pressure. The residue was applied to column chromatography (silica gel, dichloromethane/methanol or hexane/acetone or chloroform/acetone) and/or MPLC (chloroform/ethyl acetate) to give corresponding tetracyclic intermediate 12a as illustrated in FIG. 4a.

Method A: A solution of precursor 11a (78 mg, 0.25 mmol), phenyl isonitrile (129 mg, 1.25 mmol), and hexamethylditin (123 mg, 0.375 mmol) in benzene (25 mL) in a flat flask was irradiated with a 275W GE sunlamp at 80° C. for 20 hours. Solvent, isonitrile, and other volatile components were removed under reduced pressure. The residue was applied to MPLC (EM LiChroprep Si 60, chloroform/ethyl acetate=1.8/1) to give 37 mg of tetracycle 12a as illustrated in FIG. 4a. The yield was 45%.

Method B: A solution of precursor 11a (624 mg, 2 mmol), phenyl isonitrile (309 mg, 3 mmol), and hexamethylditin (982 mg, 3 mmol) in benzene (30 mL) in a flat flask was irradiated for 12 hours with a 450W Ace Hanovia lamp. After removal of solvent, isonitrile, and other volatile components under reduced pressure, the residue was applied to column chromatography (silica gel, hexane/acetone 1.3:1.1:1) to give 340 mg of crude product as brown solids. The crude product was ground with ether, filtered, and rinsed with ether to give 178 mg of tetracycle 12a as light yellow solids. The filtrate was concentrated and applied to MPLC to give additional 103 mg of tetracycle 12a, in 42% total yield.

EXAMPLE 2

Following the procedure of Example 1, method A, except para-methoxyphenyl isonitrile (166 mg, 1.25 mmol) was substituted for phenyl isonitrile. MPLC (chloroform/ethyl acetate 1:1) afforded 30 mg of tetracycle 12b (as shown in FIG. 4b) as off-white solids in 33% yield. $^1$H NMR (300 MHz, CDCl$_3$) δ8.16 (1 H, s), 8.03 (1 H, d, J=9.3 Hz), 7.40 (1 H, dd, J=9.3, 2.7 Hz), 7.21 (1 H, d, J=1.0 Hz), 7.09 (1 H, d, J=2.7 Hz), 6.58 (1 H, d, J=1.0 HZ), 5.15 (2 H, s), 3.93 (3

H, s), 3.69 (3 H, s), 3.45 (1 H, t, J=7.6 Hz), 2.11 (1 H, m), 1.90 (1 H, m), 0.93 (3 H, t, J=7.3 Hz); $^{13}$C NMR (75 MHz, CDCl$_3$) δ172.7, 161.3, 158.7, 152.7, 150.4, 146.2, 144.9, 130.9, 129.4, 123.4, 129.3, 118.7, 105.4, 100.4, 96.1, 55.6, 53.2, 52.3, 49.7, 25.6, 12.0; IR (neat) 1730, 1667, 1601, 1240 cm$^{-1}$; MS (m/e) 364 (M, base peak), 336, 305, 278; HRMS calcd for C$_{12}$H$_{20}$O$_4$N$_2$ 364.1423, found 364.1477.

EXAMPLE 3

Figure 4C:
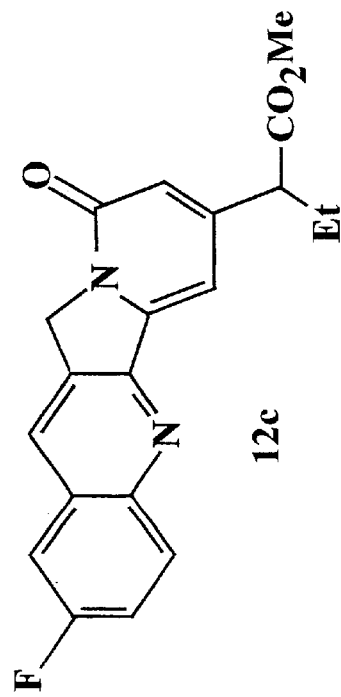

Following the procedure of Example 1, method A, except para-fluorophenyl isonitrile (151 mg, 1.25 mmol) was substituted for phenyl isonitrile. MPLC (chloroform/ethyl acetate 2:1) afforded 29 mg of tetracycle 12c (shown in FIG. 4c) as light yellow solids in 33% yield. $^1$H NMR (300 MHz, CDCl$_3$) δ8.30 (1 H, s), 8.20 (1 H, dd J=9.3, 5.4 Hz), 7.55 (2 H, m), 7.29 (1 H, d, J=1.3 Hz), 6.63 (1 H, d, J=1.3 Hz), 5.24 (2 H, s), 3.71(3 H, s), 3.48 (1 H, t, J=7.7 Hz), 2.16 (1 H, m), 1.90 (1 H, m), 0.95 (3 H, t, J=7.3 Hz); $^{13}$C NMR (75 MHz, CDCl$_3$) 8δ 172.8, 161.3, 161.2 (J$_{CF}$=250.8 Hz), 152.7, 152.5, 146.0, 145.7, 132.2 (J$_{CF}$=8.3 Hz), 130.3, 129.7, 128.9 (J$_{CF}$=10.2 Hz), 120.9 (J$_{CF}$=26.8 Hz), 119.6, 111.3 (J$_{CF}$=21.9 Hz), 100.9, 53.2, 52.4, 49.7, 25.7, 12.1; IR (neat) 1732, 1659, 1599 cm$^{-1}$; MS (m/e) 353 (M+1), 352 (M, base peak), 324, 293, 265; HRMS calcd for C$_{20}$H$_{17}$O$_3$FN$_2$ 352.1224, found 352.1248.

EXAMPLE 4

Following the procedure of Example 1, method B. A solution of 2-(6-bromo-N-(2-pentyn-1-yl)-2(1H)-pyridon-4-yl)butyrate (510 mg, 1.5 mmol) prepared from 10, parafluorophenyl isonitrile (272 mg, 2.25 mmol), and hexamethylditin (737 mg, 2.25 mmol) in benzene (22.5 mL) was irradiated for 17.5 h. Column chromatography (silica gel, hexanelacetone 1.5:1, 1:1) afforded 461 mg of crude product. The product was washed with ether to give 142 mg of tetracycle 12d (shown in FIG. 4d) as light yellow solids. The filtrate gave, after concentration and application to MPLC (chloroform/ethyl acetate 1.8:1), 54 mg of tetracycle 12d. Total yield was 33%. $^1$H NMR (300 MHz, CDCl$_3$) δ8.18 (1 H, dd, J=9.2, 5.6 Hz), 7.67 (1 H, dd, J=9.9, 2.6 Hz), 7.54 (1 H, td, J=9.2, 2.6 Hz), 7.28 (1 H, s), 6.62 (1 H, s), 5.19 (2 H, s), 3.70 (3 H, s), 3.47 (1 H, t, J=7.7 Hz), 3.10 (2 H, q, J=7.6 Hz), 2.14 (1 H, m), 1.90 (1 H, m), 1.36 (3 H, t, J=7.6 Hz), 0.94 (3 H, t, J=7.4 Hz); $^{13}$C NMR (75 MHz, CDCl$_3$) δ172.7, 161.3, 161.2 (J$_{CF}$=250.2 Hz), 152.8, 151.9, 146.4, 146.3, 144.9, 133.0 (J$_{CF}$=9.4 Hz), 127.8 (J$_{CF}$=12.0 Hz), 127.7, 120.2 (J$_{CF}$=26.3 Hz), 119.3, 107.3 (J$_{CF}$=23.4 Hz), 100.9, 53.2, 52.3, 49.0, 25.6, 23.2, 13.8, 12.0; IR (neat) 1734, 1665, 1601 cm$^{-1}$; MS (m/e) 380 (M, base peak), 352, 321, 294; HRMS calcd for C$_{22}$H$_{21}$O$_3$FN$_2$ 380.1536, found 380.1539.

EXAMPLES 5.1–5.3

Figure 4E:
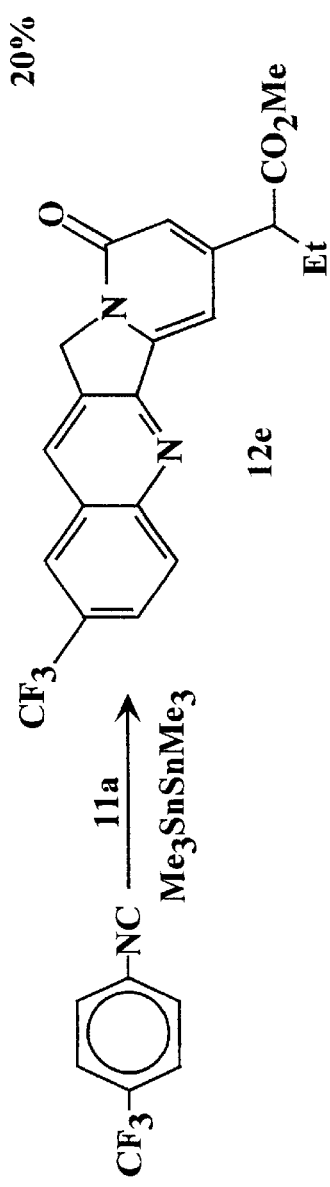
Figure 4F:
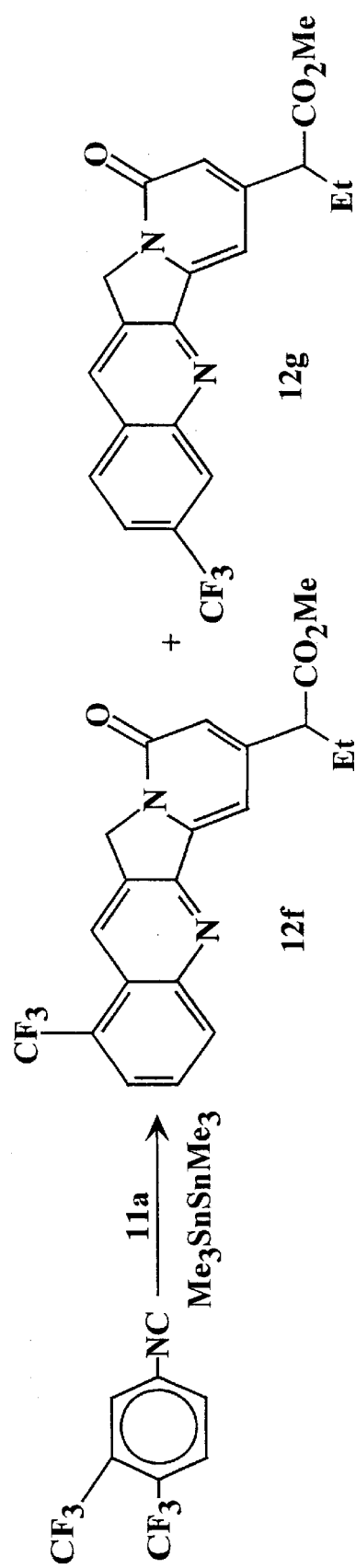
Figure 4G:
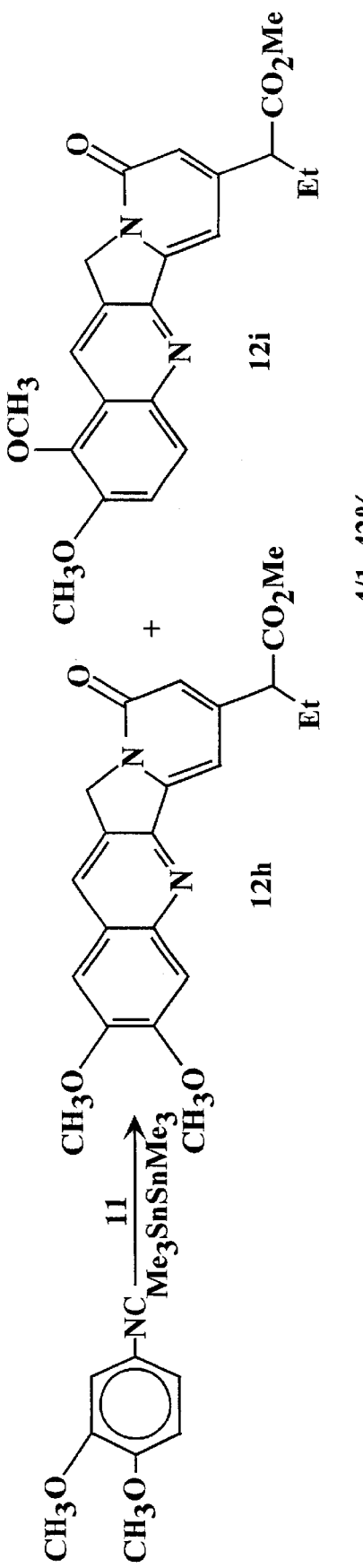

Further examples of tetracycle analogues obtained by substitution of various aryl isonitriles for phenyl isonitrlle and otherwise following the procedure set forth in Example 1, method B, are set forth in FIGS. 4e–4g. Tetracycle 12e (shown in FIG. 4e) was obtained in 20% yield. In the case of the meta-substituted isonitrile reactant shown in FIG. 4f, two isomeric tetracycles 12f and 12g were obtained in a 2:1 ratio. The combined yield was 22%. Similarly, in the case of the meta-substituted isonitrile reactant shown in FIG. 4g, two isomeric tetracycles 12h and 12i were obtained in a 4:1 ratio. The general formula of FIG. 3 illustrates such isomers as 12 and 12'. The combined yield in the case of tetracycle 12h and 12i was 42%.

EXAMPLE 5.1

Example 1, method B was followed. A solution of 11a (156 mg, 0.5 mmol), para-trifluromethylphenylisonitrile (171 mg, 1 mmol), and hexamethylditin (246 mg, 0.75 mmol) in benzene (10 mL) was irradiated for 4 to 12 h. Column chromatography (silica gel, hexane/acetone 2:1, 1:1) followed by MPLC (chloroform/ethyl acetate 3.5:1) afforded 41 mg of 12e in 20% yield. $^1$H NMR (300 MHz, CDCl$_3$) δ8.46 (1 H, s), 8.33 (1 H, d, J=8.9 Hz), 8.23 (1 H, s), 7.97 (1 H, dd, J=8.9, 1.6 Hz), 7.37 (1 H, d, J=1.0 Hz), 6.68 (1 H, d, J=1.0 Hz), 5.29 (2 H, s), 3.72 (3 H, s), 3.50 (1 H, t, J=7.7 Hz), 2.18 (1 H, m), 1.91 (1 H, m), 0.97 (3 H, t, J=7.4 Hz); $^{13}$C NMR (125 MHz, CDCl3) δ172.7, 161.2, 155.1, 152.7, 149.8, 145.3, 131.9, 131.0, 131.1, 129.5, (q, J$_{CF}$=33 Hz), 127.0, 126.2 (2 C), 123.8 (q, J$_{CF}$=271 Hz), 120.4, 101.8, 53.2, 52.5, 49.7, 25.7, 12.1: IR (neat) 1732, 1667, 1605, 1171, 1123cm$^{-1}$; MS (m/e) 403, 402 (M, base peak), 383, 374, 343, 328, 315.

EXAMPLE 5.2

Example 1, method B was followed. A solution of 11a (156 mg, 0.5 mmol), meta-trifluoromethylphenylisonitrile (171 mg, 1 mmol), and hexamethylditin (246 mg, 0.75 mmol) in benzene (10 mL) was irradiated for 12 hours. Column chromatography (silica gel, hexane/acetone 2:1, 1:1) followed by MPLC (chloroform/ethyl acetate 11:1, 2.5:1) afforded 31 mg of 12f and 12g in 22% yield. 12f: $^1$H NMR (300 MHz, CDCl$_3$) δ8.67 (1 H, s), 8.39 (1 H, d, J=8.5 Hz), 8.01 (1 H, d, J=7.3 Hz), 7.84 (1 H, t, J=7.9 Hz), 7.34 (1 H, d, J=1.4 Hz), 6.67 (1 H, d, J=1.4 Hz), 5.29 (2 H, s), 3.72 (3 H, s), 3.49 (1 H, t, J=7.7 Hz), 2.17 (1 H, m), 1.91(1 H, m), 0.96 (3 H, t, J =7.4 Hz); $^{13}$C NMR (125 MHz, CDCl$_3$) δ172.7, 161.2, 153.6, 152.7, 149.0, 145.2, 134.5, 130.3, 128.8, 127.6, 126.7 (q, J$_{CF}$=31 Hz), 126.3, 124.2, 124.0 (q, J$_{CF}$=272 Hz), 120.2, 101.5, 53.2, 52.4, 50.0, 25.7, 12.1; IR (neat) 1736, 1671, 1609, 1306, 1167, 1121 cm$^-$; MS (m/e) 403, 402 (M, base peak), 374, 343, 328, 315. 12 g: $^1$H NMR (300 MHz, CDCl$_3$) δ8.53 (1 H, s), 8.44 (1 H, s), 8.06 (1 H, d, J=8.6 Hz), 7.82 (1 H, dd, J=8.6, 1.4 Hz), 7.35 (1 H, d, J=1.4 Hz), 6.69 (1 H, d, J=1.4 Hz), 5.30 (2H, s), 3.73 (3 H, s), 3.50 (1 H, t, J=7.7 Hz), 2.18 (1 H, m), 1.92 (1 H, M), 0.97 (3 H, t, J=7.4 Hz); $^{13}$C NMR (125 MHz, CDCl$_3$) δ172.6, 161.2, 154.4, 152.8, 147.9, 145.2, 132.2 (q, J$_{CF}$=33 Hz), 131.0, 130.8, 129.4 (2 C), 127.6, 123.8 (q, J$_{CF}$=271 Hz), 123.4, 120.2, 101.7, 53.2, 52.5, 49.8, 25.7, 12.1; IR (neat) 1736, 1665, 1592, 1325, 1188, 1165, 1129 cm$^-$; MS (m/e) 403, 402 (M, base peak), 383, 374, 343, 328, 315.

EXAMPLE 5.3

Example 1, method B was followed. A solution of 11a (156 mg, 0.5 mmol), 3,4-dimethoxyphenylisonitrile (163 mg, 1 mmol), and hexamethylditin (246 mg, 0.75 mmol) in benzene (10 mL) was irradiated for 12 hours. Column chromatography (silica gel, hexane/acetone/methanol 1:1:0, 1:1:0.05) followed by MPLC (chloroform/ethyl acetate/methanol 1:1:0, 1:1:0.1) afforded 18 mg of 12i and 66 mg of 12h in 42% total yield. 12i: $^1$H NMR (300 MHz, CDCl$_3$) δ8.63 (1 H,s), 7.98 (1 H, d, J =9.4 Hz), 7.60 (1 H, d, J=9.4 Hz), 7.26 (1 H, d, J=1.5 Hz), 6.62 (1 H, d, J=1.5 Hz), 5.24 (2 H, s), 4.05 (6 H, s), 3.71 (3 H, s), 3.47 (1 H, t, J=7.8 Hz), 2.16 (1 H, m), 1.90 (1 H, m), 0.95 (3 H, t, J=7.3 Hz); $^{13}$C NMR (125 MHz, CDCl$_3$) δ172.8, 161.4, 152.7, 151.2, 149.4, 146.1, 144.4, 142.1, 128.9, 125.8, 125.0, 124.1, 119.2, 118.7, 100.7, 61.5, 56.8, 53.2, 52.4, 50.0, 25.6, 12.1, IR (neat) 1732, 1662, 1595, 1267, 1169, 1096 cm$^{-1}$; MS (m/e) 395, 394 (M, base peak), 379, 366, 335, 308; 12h: $^1$H NMR (300 MHz, CDCl$_3$) δ8.19 (1 H, s), 7.51 (1 H, s), 7.22 (1 H, d, J=1.1 Hz), 7.13 (1 H, s), 6.60 (1 H, d, J=1.1 Hz), 5.20 (2 H, s), 4.08 (3 H, s), 4.06 (3 H, s), 3.71 (3 H, s), 6.60

(1 H, d, J=1.1 Hz), 5.20 (2 H, s), 4.08 (3 H, s), 4.06 (3 H, s), 3.71 (3 H, s), 3.47 (1 H, t, J=7.7 Hz), 2.16 (1 H, m), 1.90 (1 H, m), 0.95 (3 H, t, J=7.4 Hz); $^{13}$C NMR (125 MHz, CDCl$_3$) δ172.7, 161.4, 153.3, 152.7, 150.9, 150.5, 146.5, 146.1, 128.9, 127.6, 124.3, 118.6, 107.9, 105.2, 100.1, 56.3, 56.2, 53.2, 52.3, 49.8, 25.5, 12.0; IR (neat) 1736, 1667, 1617, 1599, 1503, 1431, 1256, 1225 cm$^{-1}$; MS (m/e) 395, 394 (M, base peak), 366, 335, 320, 308.

EXAMPLE 6.1–6.3

Figure 5:
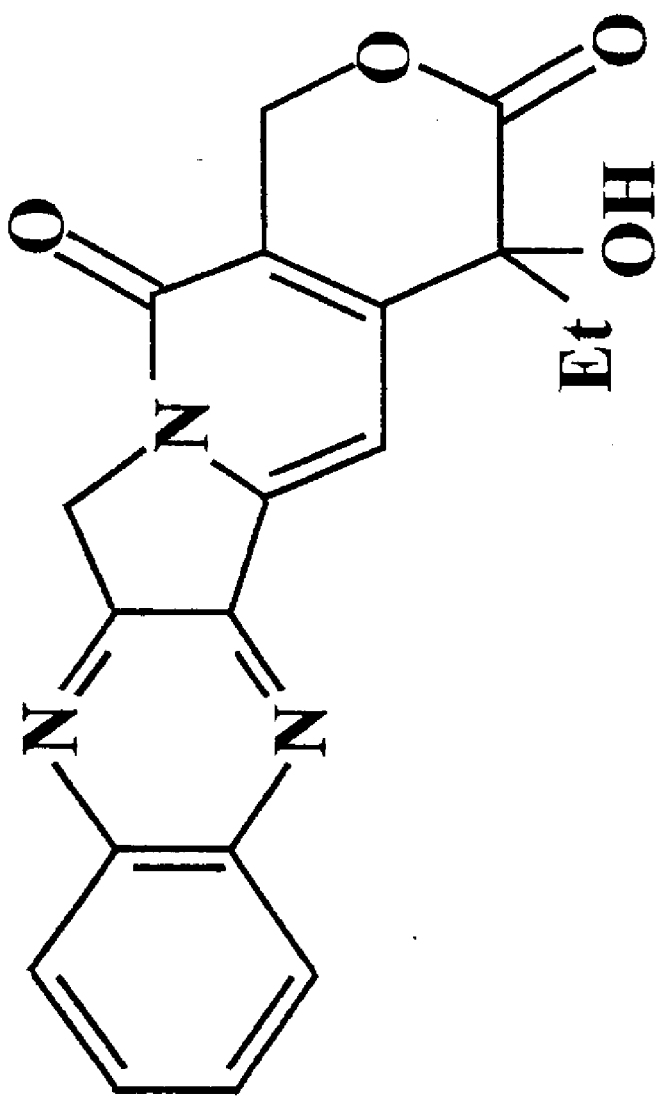
FIG. 5 is an illustration of a novel camptothecin analogue.

An interesting analogue of camptothecin potentially accessible by the present radical [4+1] annulation method is shown in FIG. 5. The quinoxaline ring system of this analogue would be formed by employing a nitrile (rather than an alkyne) as the radical acceptor Y in the pyridone precursor 11 of FIG. 3.

Several examples of synthesis of the requisite pyridinone precursors and the resulting tetracycle intermediates for the analogue of FIG. 5 and related compounds are given below.

EXAMPLE 6.1

Figure 6:
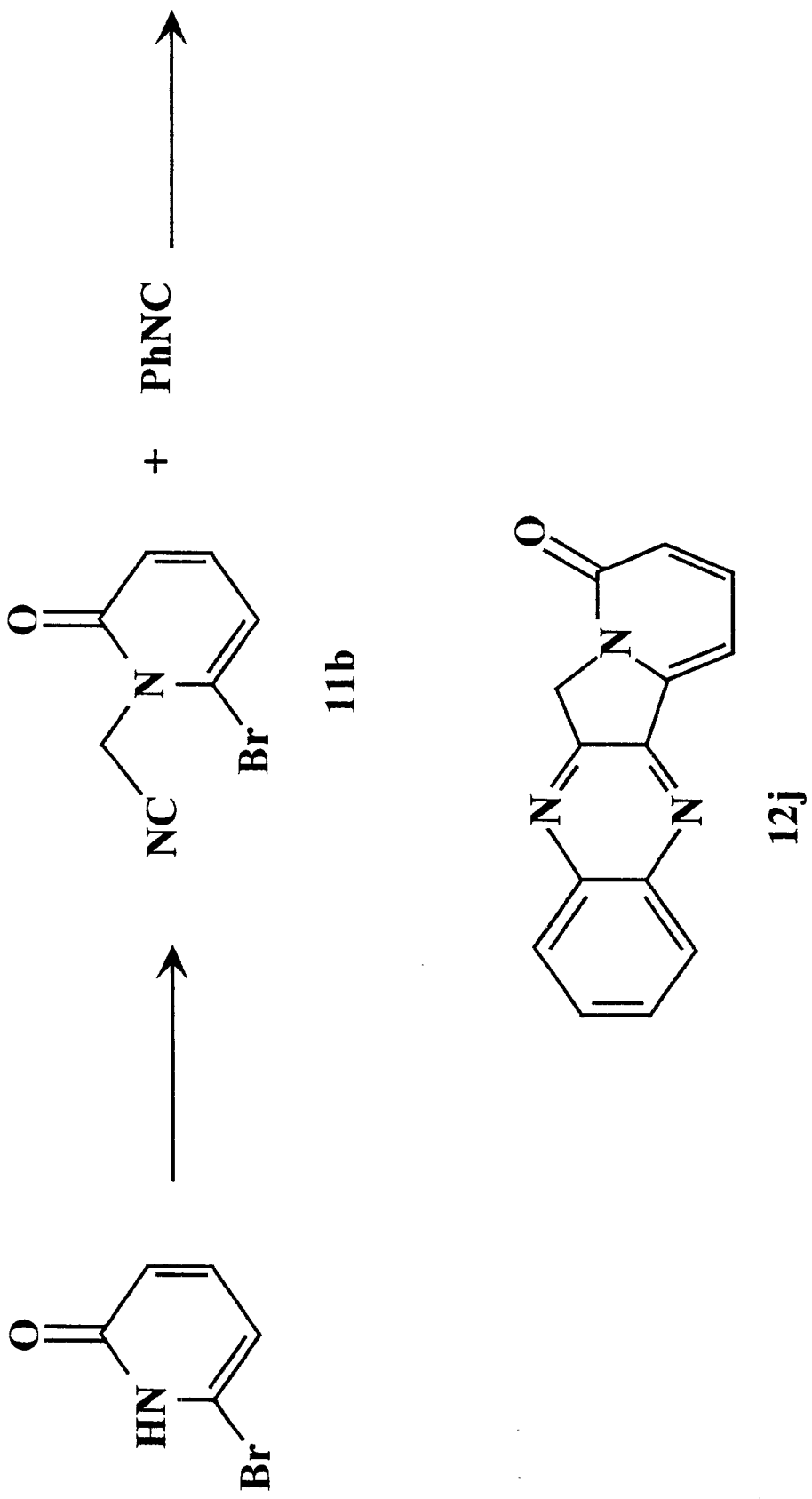
FIG. 6 provides an illustration of a model synthetic scheme for a novel tetracyclic intermediate.

The precursor 11b of FIG. 6 was produced by first cooling a solution of 6-bromopyridone (1.0 g, 5.75 mmol) in DME (20 mL) to −60° C. Sodium hydride (252 mg of a 60% dispersion in oil, washed with hexanes and dried) was then added and the mixture was allowed to warm to room temperature. The mixture was stirred for 30 mins., until H$_2$ evolution had ceased. After this time, lithium bromide (550 mg, 6.32 mmol), bromoacetonitrile (1.38 g, 11.5 mmol) and DMF (665 mL) were added. The mixture was then heated at reflux for 16 hours. The indigo-colored reaction mixture was then concentrated at reduced pressure and the residue was partitioned between CH$_2$Cl$_2$ (20 mL) and water (20 mL). The aqueous phase was further extracted with CH$_2$Cl$_2$ (3×20 mL). The combined organic extracts were then dried, filtered and concentrated at reduced pressure. Flash chromatography (eluant, 1:1 hexane, ethyl acetate) of the crude product and concentration of the fractions containing material R$_f$=0.1 afforded the product pyridone precursor 11b as a colorless solid (730 mg, 64%). This material was recrystallized from CHCl$_3$/hexane to afford colorless needles, mp 100–101° C. $^1$H NMR (300 MHz, CDCl$_3$) δ7.23 (dd, J=9.3 and 7.0 Hz, 1 H, H4), 6.58 (d, J=9.3 Hz, 1 H), 6.56 (d, J=7.0 Hz, 1 H), 5.18 (s, 2H). $^{13}$C NMR (75 MHz, CDCl$_3$) δ161.66, 140.29, 125.32, 119.18, 113.80, 111.98, 35.99. IR (KBr) 2999, 2961, 1660, 1583, 1512, 800 cm$^{-1}$. MS m/e 212, 214 (M$^+$), 184, 186 (M—CO), 133 (M±Br).

A solution of pyridone precursor 11b (100 mg, 0.469 mmol) in benzene (10 mL) containing hexamethylditin (222 mg, 0.678 mmol) and phenyl isonitrile (2.4 mL of a 1.0M solution in benzene) was heated at 80° C. and irradiated with an hanovia UV lamp for 16 hours. After this time the mixture was diluted with Et$_2$O and shaken with 2M HCl and then filtered through a sintered glass funnel. The phases were then separated and the organic phase was extracted with 2M HCl (6×20 mL). The combined aqueous acidic phases were neutralized with NaOH and extracted with CHCl$_3$ (4×50 mL). The combined organic phases were then dried, filtered and concentrated at reduced pressure to afford a brown oil (110 mg). Preparative U.C.T. of this material (1:1 acetone, CH$_2$Cl$_2$) and extraction of the yellow fluorescent band (Rf=0.5) gave the product tetracycle 12j as shown in FIG. 6 as a yellow solid (38 mg, 35%). $^1$H NMR (300 MHz, CDCl$_3$) δ8.20 (m, 2H), 7.88 (m, 2H), 7.68 (dd, J=8.7 and 7.0 Hz, 1H), 7.31 (d, J=6.7 Hz, 1H), 6.82 (d, J=8.9 Hz, 1H), 5.31 (s, 3H). $^{13}$C NMR (125 MHz, CDCl$_3$) δ161.20, 152.95, 146.65, 144.22, 142.88, 142.74, 140.14, 131.31, 130.69, 129.87, 129.48, 122.25, 102.30, 50.55. IR (KBr) 3445, 2363, 2340, 1653 cm$^{-1}$. MS m/e 235 (M$^+$), 207 (M—CO).

EXAMPLE 6.2

Figure 7:
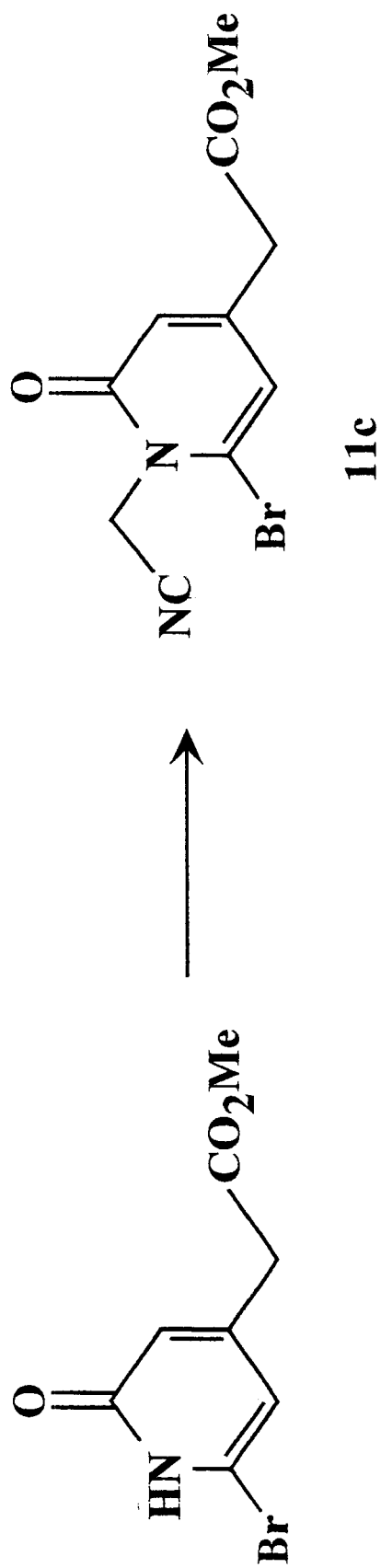
FIG. 7 provides a synthetic scheme for a novel precursor.

Precursor 11c of FIG. 7 was produced by first treating a solution of bromopyridone (1.5 g, 6.10 mmol) in DME (20 mL) at −60° C. with sodium hydride (267 mg of a 60% dispersion in oil). The mixture was allowed to warm to room temperature, and after evolution of hydrogen had ceased lithium bromide (585 mg, 6.72 mmol), bromoacetonitrile (1.46 g, 12.18 mmol) and DMF (720 ●L) were added. The mixture was then heated at reflux for 16 hours. After usual workup and chromatographic purification, the product was afforded as a colorless solid (0.98 g, 56%, 64% based on recovered starting material). This material was recrystallized from CHCl$_3$/hexanes to give colorless prisms, mp 107–109° C. $^1$H NMR (300 MHz, CDCl$_3$) δ6.57 (s, 1H), 6.47 (s, 1 H), 5.15 (s, 2 H), 3.74 (s, 3 H), 3.43 (s, 2H). $^{13}$C NMR (75 MHz, CDCl$_3$) δ169.17, 161.17, 147.67, 125.05, 118.90, 113.71, 113.58, 52.58, 40.14, 35.75. IR (KBr) 3017, 2957, 2361, 2342, 1736, 1668, 1593, 1508 cm$^{-1}$. MS m/e 284, 286 (M+), 245, 247 (M—CH$_2$N), 205 (M—Br, 100).

EXAMPLE 6.3

A solution of pyridone precursor 11c (533 mg, 1.87 mmol) in DME (8 mL) was cooled to −70° C. KO$^t$Bu (0.23 g, 2.05 mmol) was added in one portion, and the solution immediately turned a bright yellow color. After 5 mins., ethyl iodide (0.62 g, 7.75 mmol) was added and the reaction mixture was stirred for 2 hours at −70° C. and then at room temperature for 20 hours. After this time the mixture was poured into water (20 mL) and extracted with CH$_2$Cl$_2$ (3×20 mL). The combined extracts were dried, filtered and then concentrated at reduced pressure. The residue obtained was purified by flash chromatography (eluant, 1:1 ethyl acetate, CHCl$_3$) to afford the product 11d of FIG. 8 as a colorless oil that solidified on standing (400 mg, 65%). This precursor 11d was recrystallized from CHCl$_3$/hexanes to afford colorless prisms. $^1$H NMR (300 MHz, CDCl$_3$) δ6.55 (s, 1H), 6.42 (s, 1H), 5.12 (s, 2 H), 3.66 (s, 3 H), 3.21 (t, J=7.6 Hz, 1 H), 1.97 (m, 1 H), 1.68 (m, 1H), 0.87 (t, J=7.3 Hz, 3 H). $^{13}$C NMR (75 MHz, CDCl$_3$) δ171.71, 161.11, 152.28, 125.07, 117.60, 113.72, 111.84, 52.26, 35.69, 32.52, 25.08, 11.68. IR (NaCl) 2967, 2359, 1736, 1671, 1597, 1200, 1169 cm$^{-1}$, MS m/e 314, 316 (M$^+$), 233 (M—Br, 100).

Figure 8:
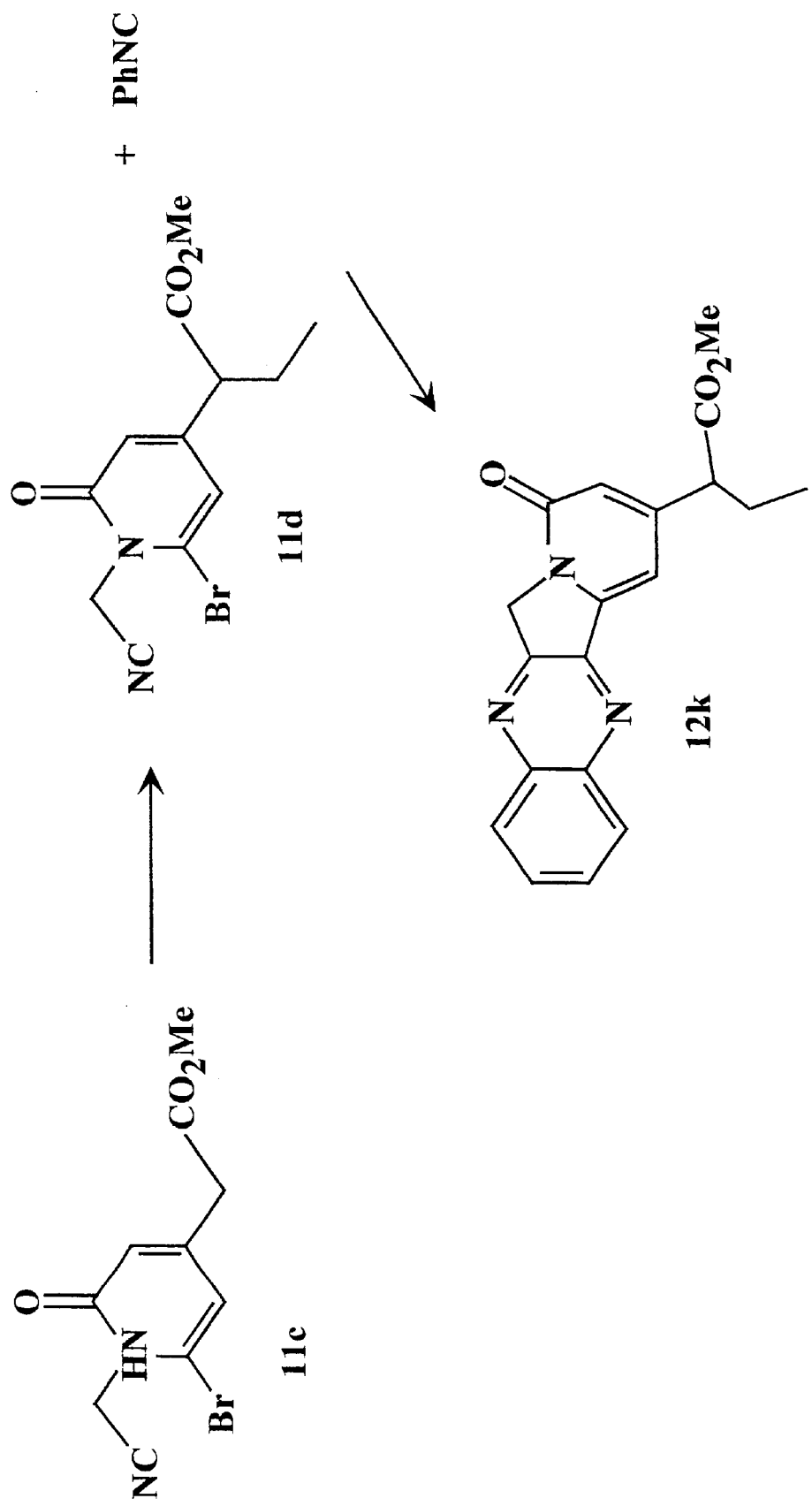
FIG. 8 provides an illustration of the synthetic scheme for a novel tetracyclic intermediate.

According to FIG. 8, a solution of the bromopyridinone precursor 11d (120 mg, 0.383 mmol), phenyl isonitrile (2.0 mL of a 1.0M solution in benzene) and hexamethylditin (180 mg) in benzene (10 mL) was heated at 80° C. and irradiated with a Hanovia lamp for 20 hours. The mixture was then concentrated and the residue was purified by flash chromatography, (EtOAc/CHCl$_3$, 1:1). Fractions containing fluorescent material, R$_f$=0.3 were combined and concentrated to afford product tetracycle 12k as a yellow solid (14 mg, 11%). $^1$H NMR (300 MHz, CDCl$_3$) δ8.20 (m, 2 H), 7.88 (m, 2 H), 7.35 (s, 1 H), 6.71 (s, 1 H), 5.28 (s, 2 H), 3.73 (s, 3 H), 3.49 (t, J=7.6 Hz, 1 H), 2.16 (m, 1 H), 1.90 (m, 1 H), 0.97 (t, J=7.3 Hz, 3 H). $^{13}$C NMR (125 MHz, CDCl$_3$) δ172.65, 160.95, 153.10, 152.42, 146.51, 143.94, 142.84, 142.74, 131.38, 130.95, 129.89, 129.48, 121.05, 102.37, 53.19, 52.50, 50.37, 25.64 (one resonance not observed). IR (NaCl) 2973, 2386, 1738, 1659, 1651, 1622 cm$^{-1}$. MS m/e 335 (M$^+$, 100), 307 (M—CO), 276 (M—CO$_2$Me).

Preparation of Aryl Isonitriles

Figure 9:
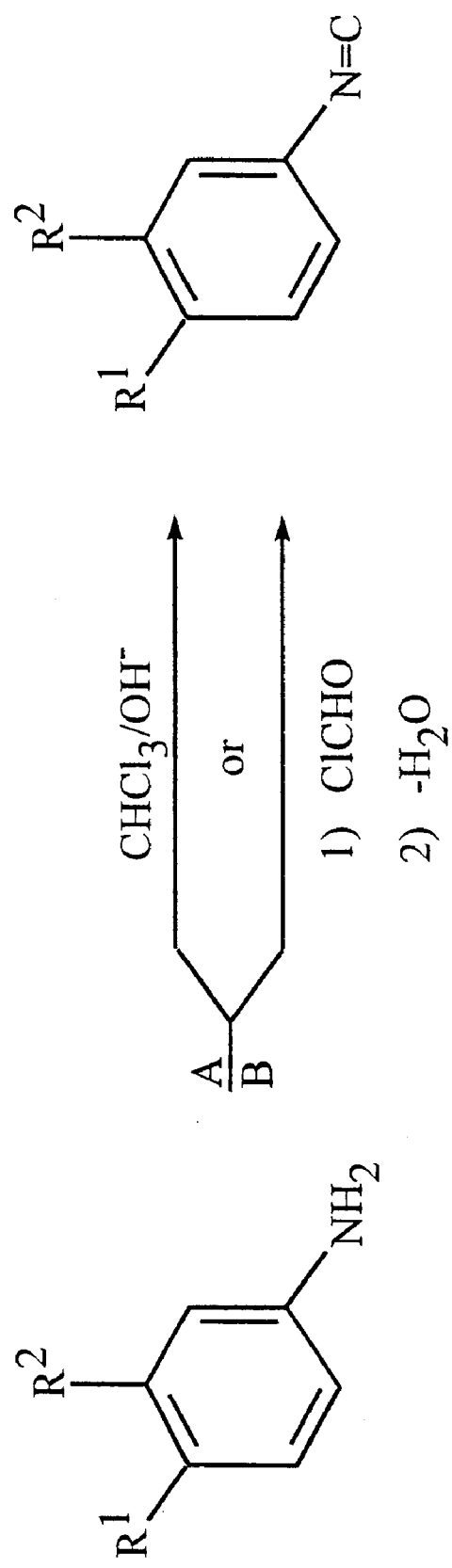
FIG. 9 provides an illustration of synthetic schemes for preparing aryl isonitriles.

The aryl isonitriles (e.g., phenyl isonitrile) for reaction with precursor 11 in the present synthesis are readily available from aryl amines by several standard methods as illustrated in FIG. 9. Typically, amines are reacted with base and chloroform (Method A of FIG. 9) or they are first converted to the respective formamides which are then dehydrated (Method B of FIG. 9). See Ugi, I., "Isonitrile Chemistry," Academic Press, NY, 10–17 (1971) and Walborsky, H., *Org. Prep. Proced. Int.*, 11, 293–311 (1979), the disclosure of which are incorporated herein by reference.

Reaction of Aryl Isonitriles with Precursor 11

The reaction of precursor 11 with an aryl isonitrile to produce a tetracycle intermediate preferably takes place in the presence of a coreactant of the general formula given below:

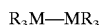

In the above general formula, M comprises a metal or metalloid. Preferably M comprises Si, Ge or Sn. Most preferably M comprises Sn. R may comprise a branched or unbranched alkyl or aryl group. Preferably, such an alkyl group is in the range of $C_1$ to $C_{10}$. Such aryl groups are preferably phenyl or napthyl groups, and more preferably phenyl groups. Although preferable, the coreactant need not be symmetrically substituted. Preferably the coreactant comprises hexamethylditin.

Several examples of the reaction of precursor 11a and phenyl isonitrile are given in Table 1 for hexabutylditin $(Bu_3Sn)_2$, hexamethyldisilane $(Me_3Si)_2$ and hexamethylditin $(Me_3Sn)_2$. The percent yields in Table 1 are for tetracycle intermediate 12a.

TABLE 1

| | Coreactant | Phenyl isonitrile | Temp. | Time | Yield |
|---|---|---|---|---|---|
| [1] | 1.5 eq $(Bu_3Sn)_2$ | 5 eq | 80° C. | 24 hr. | 48% |
| | 1.5 eq $(Bu_3Sn)_2$ | 1.5 eq | RT | 24 hr. | 35% |
| [2] | 1.5 eq $(Me_3Si)_2$ | 5 eq | 80° C. | 24 hr. | 45% |
| | 1.5 eq $(Me_3Si)_2$ | 1.5 eq | RT | 24 hr. | 28% |
| [3] | 1.5 eq $(Me_3Sn)_2$ | 5 eq | 80° C. | 36 hr. | 58% |
| | 1.5 eq $(Me_3Sn)_2$ | 1.5 eq | RT | 52 hr. | 56% |

Metal or metalloid hydrides may also be used as a coreactant.

Synthesis of Optically Active Camptothecin and Analogs Thereof

As it is believed generally that only (20S)-camptothecin and analogous enantiomers of analogs thereof are biologically active, a synthetic route to such compounds preferably enables selective synthesis of the active enantiomer.

Moreover, it has been found that the literature hydroxymethylation procedure for the novel tetracyclic intermediates described above may be difficult to develop into a commercially practical route to many pentacyclic end products. The described hydroxymethylation of the known tetracyclic 12a to provide racemic 20 deoxy camptothecin did succeed, but the isolated yields (20–25%) were lower than the reported yield (35%). See Volkmann, R. Danishefsky, S.; Eggler, J.; Soloman, D. M. *J. Am. Chem. Soc*, 93, 5576. (1971), and Liu, H., Ph.D. thesis, University of Pittsburgh (1994). Attempts to improve the literature procedure have met with little success. The use of either the literature procedure or modified procedures for the hydroxymethylations of 12b has not been found to provide significant amounts (>15%) of products.

The present invention thus provides a variant of the above 4+1 radical annulation/cyclization scheme in which the key E-ring lactone is preferably introduced in optically active form prior to the radical annulation/cyclization.

Figure 10A:
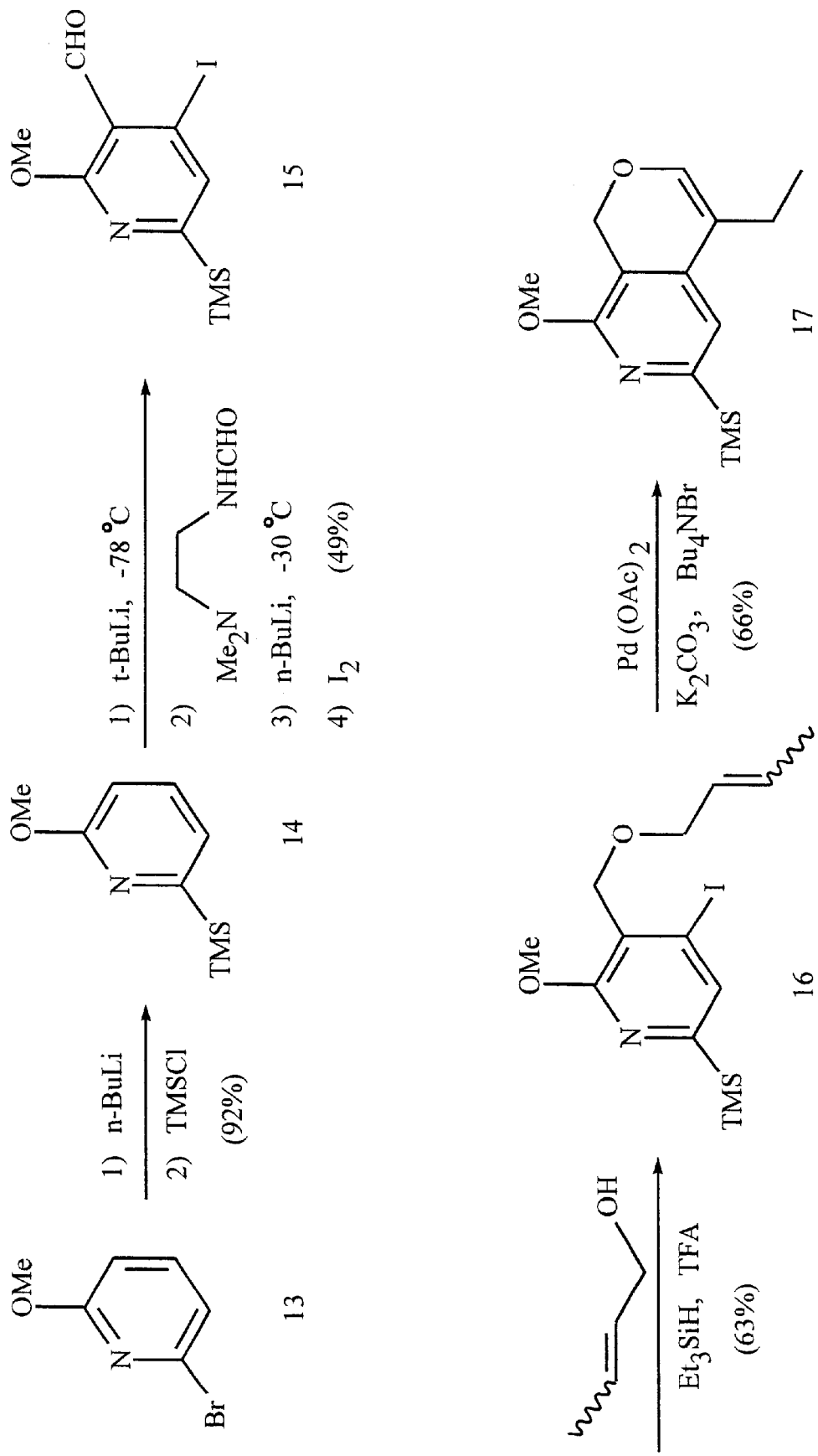
FIGS. 10a and 10b provide an illustration of the new synthetic scheme for preparation of a novel bicyclic intermediate.
Figure 10B:
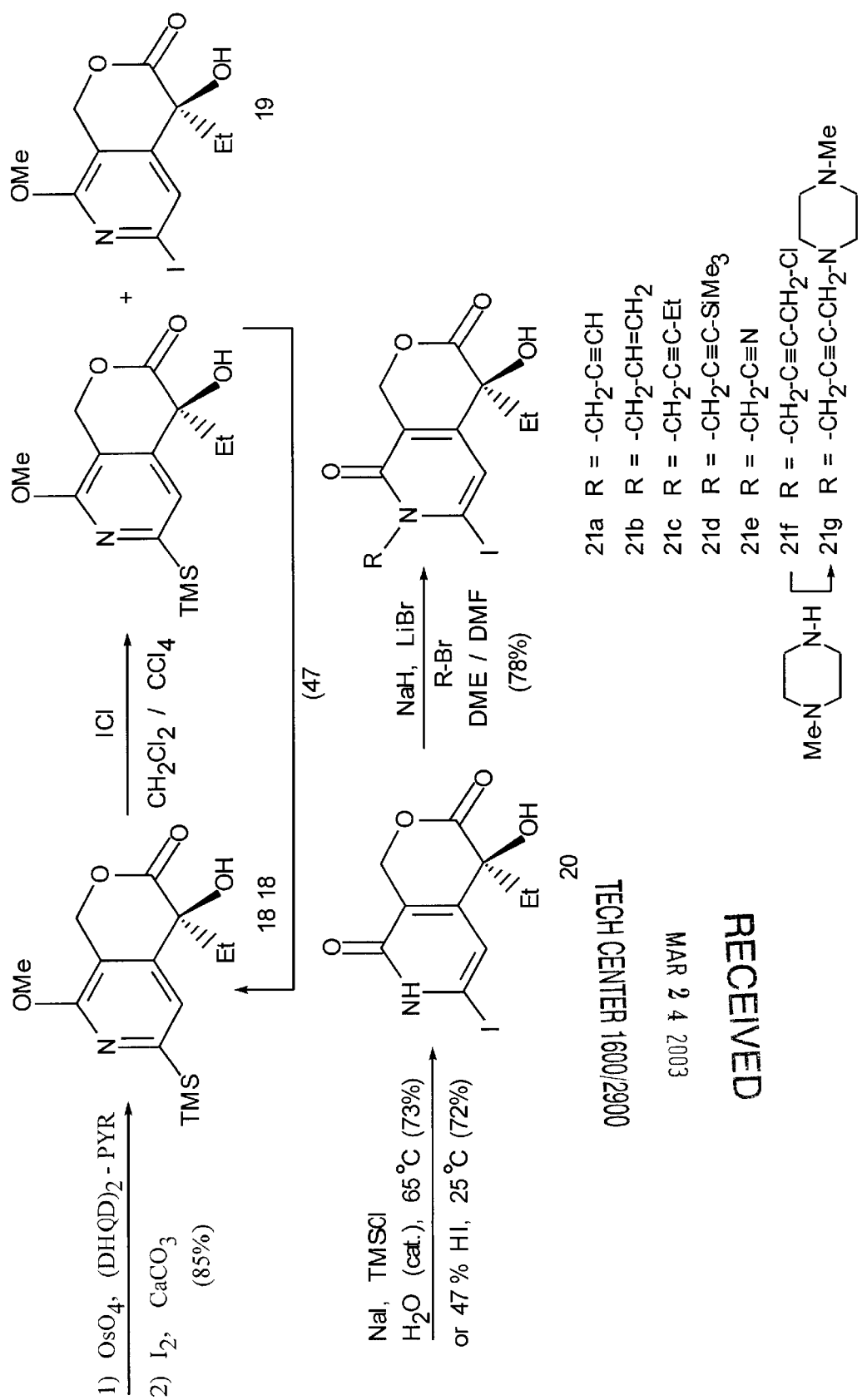

In that regard, FIGS. 10a and 10b illustrate a process for the preparation of novel bicyclic lactones 21a and 21b. In the first step, 2-methoxy-6-trimethylsilylpyridine (14) was preferably prepared from commercial 2-bromo-6-methoxypyridine (13) and chlorotrimethylsilane via classical metal-halogen exchange. See Anderson, D. G.; Webster, D. E. *J. Organomet. Chem.*, 13, 113 (1968), the disclosure of which is incorporated herein by reference. To a stirred solution of 2-bromo-6-methoxypyridine (11.28 g, 60 mmol) in anhydrous THF (120 mL) at −78° C. was added 1.6 N n-BuLi in hexanes (37.5 mL, 60 mmol). After 1 h at −78° C., a branched chlorosilane compound such as chlorotrimethylsilane (8.1 mL, 63 mmol) was added and the resulting mixture was allowed to warm to room temperature. The solution was poured into water (200 mL) and extracted with $Et_2O$ (2×100 mL). The combined organic layers were washed with brine, dried $(Na_2SO_4)$ and evaporated. The residue was distilled under reduced pressure (bp 95–100° C./15 mm Hg) to provide 10.03 g (92%) of a colorless liquid: IR (neat, $cm^{-1}$) 2953, 1566, 1452, 1416, 1282, 1242, 1026, 833; $^1H$ NMR (300 MHz, $CDCl_3$) δ0.27 (s, 9 H), 3.93 (s, 3 H), 6.62 (d, J=8.2 Hz, 1 H), 7.06 (d, J=6.6 Hz, 1 H), 7.45 (dd, J=8.2, 6.6 Hz, 1 H); $^{13}C$ NMR (300 MHz, $CDCl_3$) δ−1.8, 53.1, 110.2, 122.3, 136.8, 163.5, 165.4; HRMS (EI) m/z calcd for $C_9H_{15}NOSi$ ($M^+$) 181.0923, found 181.0929; LRMS (EI) m/z 181 ($M^+$, 6), 166 (16), 150 (6).

The preparation of 4-iodo-2-methoxy-6-trimethylsilyl-3-pyridine-carboxaldehyde (15) preferably involved a one-flask sequential directed lithiation. See Comins, D. L.; Baevsky, M. F.; Hong, H. *J. Am. Chem. Soc.*, 114, 10971 (1992); and Comins, D. L. *Synlett*, 615 (1992), the disclosures of which are incorporated herein by reference. To a stirred solution of pyridine 14 (9.07 g, 50 mmol) in anhydrous THF (150 mL) at −78° C. was added 1.7N t-BuLi in pentane (31 mL, 52.5 mmol). After 1 h, N,N,N'-trimethyl-N'-formylethylenediamine (6.83 g, 52.5 mmol) was slowly added. The reaction was allowed to warm to 40° C., 1.6N n-BuLi in hexane (63 mL, 100 mmol) was injected, and the mixture was stirred for 3 h at −30° C. A solution of 12 (30.5 g, 120 mmol) in anhydrous THF (200 mL) was then quickly added at −78° C. with vigorous stirring. The resulting mixture was allowed to warm to 0° C. (1 h), poured into 5% $Na_2SO_3$ (500 mL) and extracted with $Et_2O$ (3×300 mL). The combined organic layers were washed with half-brine and brine, and dried $(MgSO_4)$. The residue obtained after removal of the solvents was subjected to flash chromatography (hexane/AcOEt 95:5) to provide 8.20 g (49%) of a yellow oil: IR (neat, $cm^{-1}$) 2928, 1684, 1530, 1505, 1437, 1401, 1321, 1239, 1011, 828; $^1H$ NMR (300 MHz, $CDCl_3$) δ0.27 (s, 9 H), 4.03 (s, 3 H), 7.66 (s, 1 H), 10.17 (s, 1 H); $^{13}C$ NMR (300 MHz, $CDCl_3$) δ−2.1, 54.0, 108.4, 118.0, 135.5, 173.0, 191.1; HRMS (EI) m/z calcd for $C_{10}H_{14}INO_2Si$ ($M^+$) 334.9839, found 334.9833; LRMS (EI) m/z 335 ($M^+$, 60), 320 (100), 306 (13), 292 (20).

A reductive etherification of the aldehyde 15 was then performed to afford the 3-crotyloxymethyl-4iodo-2-methoxy-6-trimethylsilylpyridine 16. See Doyle, M. P.; DeBruyn, D. J.; Kooistra, D. A. *J. Am. Chem. Soc.*, 94, 3659 (1972), the disclosure of which is incorporated herein by reference. Crotyl alcohol (4.3 mL, 50 mmol), triethylsilane (4.8 mL, 30 mmol), and TFA (7.7 mL, 100 mmol) were successively added to a stirred solution of pyridinecarboxaldehyde 15 (5.05 g, 15 mmol) in anhydrous $CH_2Cl_2$ (15 mL) at 0° C. After 10 h at room temperature, the reaction mixture was slowly poured in saturated $NaHCO_3$ and the organic layer was washed with brine and dried (MgSO$_4$). The residue obtained after solvent removal was purified by flash-chromatography (hexane/AcOEt 95:5) to afford 3.71 g (63%) of a slightly yellow oil: IR (neat, cm$^{-1}$) 2942, 1551, 1520, 1446, 1333, 1240, 1084, 1022, 837, 750; $^1$H NMR (300 MHz, CDCl$_3$) δ0.24 (s, 9 H), 1.69 (dd, J=6.1, 1.0 Hz, 3 H), 3.85–4.05 (m, 2 H), 3.93 (s, 3 H), 4.55 (s, 2 H), 5.55–5.83 (m, 2 H), 7.47 (s, 1 H); $^{13}$C NMR (300 MHz, CDCl$_3$) δ–2.0, 17.9, 53.8, 69.7, 71.7, 114.0, 127.8, 129.8, 133.2, 161.5; HRMS (EI) m/z calcd for C$_{13}$H$_{19}$INO$_2$Si (M—CH$_3$$^+$) 376.0230, found 376.0239; LRMS (EI) m/z 335 (56), 320 (100), 292 (38).

The crotyl ether 16 was then subjected to a Heck reaction under standard conditions to provide 4ethyl-8-methoxy-6-trimethylsilyl-1H-3-pyreno[3,4-c]pyridine (17). See Grigg, R.; Sridharan, V.; Stevenson, P.; Sukirthalingam, S.; Worakunm, T. *Tetrahedron*, 46, 4003 (1990) and Fang, F. G.; Xie, S. P.; Lowery, M. W. *J. Org. Chem.*, 59, 6142 (1994), the disclosure of which are incorporated herein by reference. A mixture of pyridine 16 (3.44 g, 8.80 mmol), tetrabutylammonium bromide (2.84 g, 8.80 mmol), anhydrous K$_2$CO$_3$ (2.44 g, 17.60 mmol) and Pd(OAc)$_2$ (200 mg, 0.88 mmol) in anhydrous DMF (500 mL) was stirred at 85° C. for 18 h. The final solution was diluted with Et$_2$O (600 mL), filtered through a pad of Celite, washed with water (4×300 mL) and dried (MgSO$_4$). After concentration under reduced pressure, the crude product was subjected to flash-chromatography (hexane/AcOEt 95.5) to provide 1.59 g (69%) of a colorless oil: IR (neat, cm$^{-1}$) 2944, 1620, 1570, 1534, 1443, 1333, 1237, 1146, 957, 928; $^1$H NMR (300 MHz, CDCl$_3$) δ0.26 (s, 9 H), 1.12 (t, J=7.3 Hz, 3 H), 2.31 (dq, J=7.3, 1.0 Hz, 2 H), 3.94 (s, 3 H), 5.00 (s, 2 H), 6.51 (t, J=1.0 Hz, 1 H), 6.83 (s, 1 H); $^{13}$C NMR (300 MHz, CDCl$_3$) δ–1.8, 13.6, 20.8, 53.1, 62.7, 108.4, 114.5, 115.9, 139.0, 145.0, 158.7, 164.5; HRMS (EI) m/z calcd for C$_{14}$H$_{21}$NO$_2$Si (M$^+$) 263.1342, found 243.1342; LRMS (EI) m/z 263 (M$^+$, 40), 248 (100), 217 (21), 189 (16), 166 (11).

The enol ether 17 was then subjected to a standard Sharpless asymmetric dihydroxylation and the resulting crude α-hydroxy hemiketal was directly oxidized to the hydroxylactone (S)-4-ethyl-4-hydroxy-8-methoxy-3-oxo-6-trimethylsilyl-1H-pyrano[3,4-c]pyridine (18). See Curran, D. P.; Ko, S-B. *J. Org. Chem.*, 59, 6139 (1994); Fang, F. G.; Xie, S. P.; Lowery, M. W. *J. Org. Chem.*, 59, 6142 (1994); Sharpless, K. B., Chem. Rev., 94, 2483 (1994); Crispino, G. A.; Jeong, K. S.; Kolb, H. C.; Wang, Z. M.; Xu, D.; Sharpless, K. B. *J. Org. Chem.*, 58, 3785 (1993), and Corey, E. J.; Ghosh, A. K. *Tetrahedron Lett*, 29, 3205. (1988), the disclosures of which are incorporated herein by reference.

To a vigorously stirred solution of K$_3$Fe(CN)$_6$ (16.3 g, 49.5 mmol), K$_2$CO$_3$ (6.86 g, 49.5 mmol), CH$_3$SO$_2$NH$_2$ (3.1 g, 31.7 mmol), (DHQD)$_2$—PYR (0.36 g, 0.41 mmol, 2.5 mol %), and OsO$_4$ (0.1 mL of a 2.5 w % in tert-BuOH, 0.5 mol %) in 1:1 tert-BuOH/H$_2$O (160 mL) at 0° C. was added the enol ether 17 (4.28 g, 16.3 mmol). The reaction mixture was stirred for 12 hr, and then Na$_2$SO$_3$ (16.0 g) was slowly added. After 30 min, CH$_2$Cl$_2$ (100 mL) and water (100 mL) were added, and the aqueous layer was further extracted with CH$_2$Cl$_2$ (50 mL). The combined organic layers were dried over anhydrous MgSO$_4$ and then concentrated to give a residue. Flash column chromatography (CH$_2$Cl$_2$/AcOEt 5:1) gave the product, an α-hydroxylactol, as a white solid. This solid was dissolved in CH$_3$OH/H$_2$O 10:1 (300 mL), and crystalline iodine (37.1 g, 0.15 mol, 9 equiv) and CaCO$_3$ (3.3 g, 32.5 mol, 2 equiv) were added. The reaction mixture was stirred for 32 h at room temperature. Diethyl ether (300 mL), water (300 mL) and Na$_2$SO$_3$ (20 g) were then successively added to the reaction mixture. The organic layer was separated, and dried over MgSO$_4$. Flash column chromatography (hexanes/AcOEt 5:1) afforded 4.1 g (85%) of α-hydroxylactone 18: 94% ee by NMR shift experiment (Eu(hfc)$_3$); [α]$^{20}_D$ +78.3 (c 0.367, CH$_2$Cl$_2$); $^1$H NMR (300 MHz, CDCl$_3$) δ0.29 (s, 9 H), 0.96 (t, J=7.4 Hz, 3 H), 1.79 (q, J=7.4 Hz, 2H), 3.65 (s, 1 H), 4.00 (s, 3 H), 5.25 (d, J=15.6 Hz, 1 H), 5.56 (d, J=15.6 Hz, 1 H), 7.35 (s, 1 H); $^{13}$C NMR (300 MHz, CDCl$_3$) δ–1.9, 7.8, 31.9, 53.4, 66.0, 73.0, 110.5, 118.0, 146.1, 150.0, 166.5, 174.6; HRMS (EI) m/z calcd for C$_{14}$H$_{21}$NO$_4$Si (M$^+$) 295.1240, found 295.1237; LRMS (EI) m/z 295 (M$^+$, 24), 280 (55), 267 (20), 236 (26), 178 (14).

An iododesilylation of 18 provided (S)-4-ethyl-4-hydroxy-6-iodo-8-methoxy-3-oxo-1H-pyrano[3,4c]pyridine (19) in the following step. See Chou, S-S. P.; Kuo, H. L.; Wang, C. J.; Tsai, C. Y.; Sun, C. M. *J. Org. Chem.*, 54, 868 (1989); Earl, R. A.; Vollhardt, P. C. *J. Org. Chem.*, 49, 4786 (1984), the disclosures of which are incorporated herein by reference. A solution of iodine monochloride (3.24 g, 20 mmol) in anhydrous CCl$_4$ (14 mL) was added to the hydroxylactone 18 (1.48 g, 5 mmol) in anhydrous CH$_2$Cl$_2$ (20 mL) at 0° C., then the reaction mixture was stirred in the dark for 48 h at room temperature. The final solution was poured with vigorous stirring in ice-cooled 5% Na$_2$SO$_3$/brine 1:1 (300 mL) and extracted with AcOEt (3×150 mL). The combined organic layers were dried (MgSO$_4$) and concentrated under reduced pressure, and the residue was subjected to flash-chromatography (hexane/AcOEt 85:15) to afford, in order of elution, first the starting material 18 (0.70 g, 47%) and the iodo-derivative 19 (0.79 g, 45%) as a white solid: [α]$^{20}_D$ +34.0 (c 1, CHCl$_3$); IR (neat, cm$^{-1}$) 3449, 2940, 1730, 1572, 1447, 1356, 1149, 1088, 868, 752; $^1$H NMR (300 MHz, CDCl$_3$) δ0.93 (t, J =7.3 Hz, 3 H), 1.72 (q, J=7.3 Hz, 2 H), 3.65 (br s, 1 H), 3.94 (s, 3 H), 5.15 (d, J=15.6 Hz, 1 H), 5.46 (d, J=15.6 Hz, 1 H), 7.58 (s, 1 H); $^{13}$C NMR (300 MHz, CDCl$_3$) δ7.7, 31.6, 54.8, 65.4, 72.8, 110.6, 113.5, 124.0, 149.5, 157.9, 173.7; HRMS (EI) m/z calcd for C$_{11}$H$_{12}$INO$_4$ (M$^+$) 348.9811, found 348.9819; LRMS (EI) m/z 349 (M$^+$, 100), 320 (58), 305 (100), 276 (86), 178 (45). The starting material was recycled in a subsequent iododesilylation reaction.

The methyl ether function of 19 was then cleaved by iodotrimethylsilane generated in situ to give (S)-4-ethyl-4-hydroxy-6-iodo-3-oxo-1H-pyrano[3,4-c]-8-pyridone 20. See Olah, G. A.; Narang, S. C.; Gupta, B. G. B.; Malhotra, R. *J. Org. Chem.* 1979, 44, 1247, the disclosure of which is incorporated herein by reference. To a stirred solution of iodopyridine 19 (0.75 g, 2.15 mmol) and sodium iodide (0.52 g, 3.45 mmol) in anhydrous CH$_3$CN (7 mL) was slowly added chlorotrimethylsilane (0.45 mL, 3.45 mmol), followed after 15 min by water (19 μL, 1.05 mmol). The mixture was heated at 65° C. for 5 h, poured in 5% Na$_2$SO$_3$/brine 1:1 (50 mL) and quickly extracted with AcOEt (4×50 mL). After drying (MgSO$_4$) and removal of the solvents, the residue was purified by flash-chromatography (CHCl$_3$/MeOH 9:1) and recrystallized (CHCl$_3$/MeOH) to provide 525 mg (73%) of a white solid: [α]$^{20}_D$ +49.9 (c 1, MeOH); $^1$H NMR (300 MHz, CDCl$_3$) δ0.95 (t, J=7.3 Hz, 3 H), 1.77 (dq, 2 H), 4.12 (br s, 1 H), 5.14 (d, J=15.4 Hz, 1 H), 5.55 (d, J=15.4 Hz, 1 H), 7.06 (s, 1 H); $^{13}$C NMR (300 MHz, CDCl$_3$/CD$_3$OD 4:1) δ7.2, 31.0, 65.3, 72.0, 95.1, 115.3, 117.3, 150.7, 160.4, 173.2; HRMS (EI) m/z calcd for C$_{10}$H$_{10}$INO$_4$ (M$^+$) 334.9655, found 334.9656; LRMS (EI) m/z 335 (M$^+$, 57), 306 (24), 291 (100), 262 (66), 234 (44).

Alternatively, the methyl ether function of 19 could be cleaved with 47% hydriodic acid in ethyl acetate. To a solution of 19 (2.49 g, 70.13 mmol) in AcOEt (10 mL) was added 47% HI (3.5 mL, 21.4 mmol), and the reaction mixture was stirred overnight at room temperature. The final solution was slowly poured into ice-cold saturated NaHCO$_3$ (100 ml), diluted with brine (100 ml) and extracted with AcOEt (8×50 ml). After drying (MgSO$_4$) and removal of the solvent, the residue was purified as above to give 1.71 g (72%) of 20.

(S)-4-Ethyl-4-hydroxy-6-iodo-3-oxo-7-propargyl-1H-pyrano[3,4-c]-8-pyridone (21a) was prepared by a selective N-alkylation procedure that is similar to that described above in the preparation of racemic camptothecin and analogs thereof. The addition of lithium bromide or a similar lithium salt is preferable for minimization of the O-alkylation product. To a solution of iodopyridone 20 (322 mg, 0.96 mmol) in anhydrous DME (3 mL) and DMF (1 mL) at 0° C. under argon was added 60% sodium hydride in mineral oil (43 mg, 1.06 mmol). Lithium bromide (165 mg, 1.92 mmol) was added 10 min latter. After 15 min at room temperature, 80% propargylbromide in toluene (0.36 mL, 2.88 mmol) was injected and the reaction mixture was heated at 70° C. for 20 h. The final solution was poured in brine (20 mL), extracted with AcOEt (6×15 mL) and dried (MgSO$_4$). The residue obtained after removal of the solvents was subjected to flash-chromatography (CHCl$_3$/AcOEt 85:15) to give 280 mg (78%) of 21a as a foam: $[\alpha]^{20}_D$ +59.1 (c 1, CHCl$_3$); IR (neat, cm$^-$) 3381, 3278, 1738, 1644, 1595, 1527, 1225, 1134, 1041, 752; $^1$H NMR (300 MHz, CDCl$_3$) δ0.95 (t, J=7.3 Hz, 3 H), 1.75 (dq, 2 H), 2.35 (t, J=2.5 Hz, 1 H), 3.69 (br s, 1 H), 5.07 (AB system, J=16.3 Hz, 2 H), 5.10 (d, J=16.4 Hz, 1 H), 5.48 (d, J=16.4 Hz, 1 H), 7.17 (s, 1 H); $^{13}$C NMR (300 MHz, CDCl$_3$) δ7.8, 31.6, 44.0, 66.2, 71.9, 73.6, 100.2, 116.8, 118.3, 148.9, 158.2, 173.2; HRMS (EI) m/z calcd for C$_{13}$H$_{12}$INO$_4$ (M$^+$) 372.9811, found 372.9809; LRMS (EI) m/z 373 (M$^+$, 100), 344 (27), 329 (25), 217 (17).

Similar procedures can be used to make related N-propargyl- and N-allyl lactones as set forth in the following examples:

EXAMPLE 7.1

(S)-4-Ethyl-4-hydroxy-6-iodo-3-oxo-7-allyl-1H-pyrano[3,4-c]-8-pyridone (21b). The N-alkylation procedure described above for the synthesis of 21a was followed, starting from 20 (50.0 mg, 0.149 mmol) and allylbromide (40 mL, 0.45 mmol) to provide, after flash-chromatography (CHCl$_3$/AcOEt 90:10), 46.1 mg (83%) of 21b as an oil: $[\alpha]^{20}_D$ +51.9 (c 1, CHCl$_3$); IR (neat, cm$^{-1}$) 3366, 2917, 1732, 1634, 1518, 1422, 1221, 1148, 1039, 749; $^1$H NMR (300 MHz, CDCl$_3$) δ0.95 (t, J=7.4 Hz, 3 H), 1.76 (m, 2 H), 3.70 (s, 1 H), 4.94 (m, 2 H), 5.09 (d, J=16.3 Hz, 1 H), 5.18 (br d, J=16.7 Hz, 1 H), 5.29 (br d, J=10.4 Hz, 1 H), 5.47 (d, J=16.3 Hz, 1 H), 5.89 (dd, J=16.7, 10.4 Hz, 1 H), 7.15 (s, 1 H); $^{13}$C NMR (300 MHz, CDCl$_3$) δ7.7, 31.5, 56.1, 66.3, 71.8, 101.2, 116.3, 118.1, 118.7, 130.5, 148.7, 158.2, 173.3; HRMS (EI) m/z calcd for C$_{13}$H$_{14}$INO$_4$ (M$^+$) 374.9968, found 374.9951; LRMS (EI) m/z 375 (M$^+$, 100), 360 (68), 346 (15), 316 (16), 248 (23).

EXAMPLE 7.2

(S)-4-Ethyl-4-hydroxy-6-iodo-3-oxo-7-(2-pentynyl)-1H-pyrano[3,4-c]-8-pyridone (21c). The procedure described above for the synthesis of 21a was followed, starting from 20 (10 mg, 0.30 mmol) and 2-pentynyl bromide (140 mg, 0.48 mmol) to give, after flash-chromatography (CH$_2$Cl$_2$/AcOEt 8:1), 80 mg (67%) of 21c as an oil: IR (neat, cm-1) 3429, 2978, 2937, 1748, 1645, 1531, 1140; $^1$H NMR (300 MHz, CDCl$_3$) δ0.93 (t, J=7.35 Hz, 3 H), 1.09 (t, J=7.53 Hz, 3 H), 1.78 (m, 2 H), 2.12 (m, 2 H), 3.91 (s, 2 H), 5.03 (m, 2H), 5.09 (d, J=16.3 Hz, 1 H), 5.46 (d, J=16.3 Hz, 1 H), 7.16 (s, 1 H); $^{13}$C NMR (300 MHz, CDCl$_3$) δ7.7, 12.5, 13.4, 31.5, 44.5, 71.8, 72.3, 87.3, 100.4, 116.5, 118.2, 148.6, 173.2; HRMS (EI) m/z calcd for C$_{15}$H$_{16}$INO$_4$ (M$^+$) 401.0124, found 401.0123.

EXAMPLE 7.3

(S)-4-Ethyl-4-hydroxy-6-iodo-3-oxo-7-(3-trimethylsilyl-2-propynyl)-1H-pyrano[3,4-c]-8-pyridone (21d). Following the procedure described above for the synthesis of 21a, 20 (54.4 mg, 0.162 mmol) and 3-trimethylsilyl-2-propynyl bromide (93 mg, 0.49 mmol) afforded, after flash-chromatography (CHCl$_3$/AcOEt 95:5), 40.5 mg (56%) of (21d) as a foam: $[\alpha]^{20}_D$36.7 (c 1, CHCl$_3$); IR (neat, cm$^{-1}$) 3384, 2940, 2166, 1730, 1634, 1518, 1406, 1130, 841, 752; $^1$H NMR (300 MHz, CDCl$_3$) δ0.14 (s, 9 H), 0.95 (t, J=7.4 Hz, 3 H), 1.77 (m, 2 H), 3.66 (s, 1 H), 5.00 (d, J=17.2 Hz, 1 H), 5.10 (d, J=16.4 Hz, 1 H), 5.15 (d, J=17.2 Hz, 1 H), 5.49 (d, J=16.4 Hz, 1 H), 7.16 (s, 1 H); $^{13}$C NMR (300 MHz, CDCl$_3$) δ−0.40, 7.7, 31.5, 44.5, 66.3, 71.8, 90.9, 97.9, 116.5, 118.1, 148.6, 157.9, 173.3; HRMS (EI) m/z calcd for C$_{16}$H$_{20}$INO$_4$Si (M$^+$) 445.0206, found 445.0203; LRMS (EI) m/z 445 (M$^+$, 100), 430 (19), 416 (47), 386

EXAMPLE 7.4

(S)-4-Ethyl-4-hydroxy-6-iodo-3-oxo-7-(cyanomethyl)-1H-p yrano[3,4-c]-8-pyridone (21e). The procedure described above for the synthesis of 21a was followed, starting from 20 (60.0 mg, 0.179 mmol) and bromoacetonitrile (38 mL, 0.54 mmol) to provide, after flash-chromatography (CHCl$_3$/AcOEt 6:4), 49.3 mg (74%) of 21e as an oil: $[\alpha]^{20}_D$+53.0 (c 1, CHCl$_3$); $^1$H NMR (300 MHz, CDCl$_3$) δ0.96 (t, J=7.3 Hz, 3 H), 1.77 (m, 2 H), 3.78 (brs, 1 H), 5.10 (d, J=16.5 Hz, 1 H), 5.13 (d, J=17.0 Hz, 1 H), 5.27 (d, J=17.0 Hz, 1 H), 5.45 (d, J=16.5 Hz, 1 H), 7.22 (s, 1 H); $^{13}$C NMR (300 MHz, CDCl$_3$) δ7.6, 31.5, 41.7, 65.8, 98.8, 113.5, 117.3, 118.5, 149.8, 157.7, 172.8; HRMS (EI) m/z calcd for C$_{12}$H$_{11}$N$_2$IO$_4$ (M$^+$) 373.9764, found 373.9791; LRMS (EI) m/z 374 (M$^+$, 100), 345 (27), 330 (76), 290 (17), 203 (64), 191 (30), 163 (72).

EXAMPLE 7.5

(S)-4-Ethyl-4-hydroxy-6-iodo-3-oxo-7-(4-chloro-2-butyny l)-1H-pyrano[3,4-c]-8-pyridone 21f. The procedure described above for the synthesis of 21a was followed, starting from 20 (250 mg, 0.75 mmol) and 1,4-dichloro-2-butyne (275 mg, 2.24 mmol) to provide, after flash-chromatography (CH$_2$Cl$_2$/AcOEt 8:2), 200 mg (63%) of 21f (along with 42 mg (13%) of O-alkylated product): IR (neat, cm$^{-1}$) 3370, 2980, 1745, 1646, 1529, 1140; $^1$H NMR (300 MHz, CDCl$_3$) δ0.92 (t, J=7.4 Hz, 3 H), 1.77 (m, 2 H), 3.90 (s, 1 H), 4.11 (t, J=1.8 Hz, 2 H), 5.10 (d, J=16.4 Hz, 1 H), 5.13 (t, J=1.8 Hz, 2 H), 5.46 (d, J=16.4 Hz, 1 H), 7.18 (s, 1 H); $^{13}$C NMR (300 MHz, CDCl$_3$) δ7.7, 30.2, 31.6, 44.1, 66.2, 71.9, 79.6, 79.9, 100.0, 116.7, 118.3, 148.9, 158.0, 173.13.

The chloro derivative 21f is subsequently alkylated with N-methylpiperazine to give (S)-4-Ethyl-4-hydroxy-6-iodo-3-oxo-7-(4-methylpyrazinomethyl)-1H-pyrano[3,4-c]-8-pyridone 21g. The reaction mixture of 21f (180 mg, 0.43 mmol), N-methylpiperazine (130 mg, 1.30 mmol), and Bu$_4$NI (16 mg, 0.043 mmol) in DME (3 mL) was stirred for 8 hr. DME and excess N-methylpiperazine were removed and the residue was subjected to column chromatography (CH$_2$Cl$_2$/MeOH 5:1) to 185 mg (88) of 21g: IR (neat, cm$^-$) 2911, 1732, 1644, 1636, 1520, 1449, 1439, 1414, 1130, 727; $^1$H NMR (300 MHz, CDCl$_3$) δ0.97 (t, J=7.3 Hz, 3 H), 1.78 (m, 2 H), 2.34 (s, 3 H), 2.67 (br s,4 H), 3.31 (t, J=1.7 Hz, 2 H), 5.11 (d, J=16.4 Hz, 1 H), 5.12 (t, J=1.8 Hz, 2 H), 5.49 (d, J=16.4 Hz, 1 H), 7.16 (s, 1 H); $^{13}$C NMR (300 MHz, CDCl$_3$) δ7.8, 31.6, 44.3, 45.9, 47.1, 51.7, 54.9, 66.4, 71.9, 78.5, 80.5, 100.9, 116.5, 118.2, 148.8, 158.1, 173.3; HRMS (EI) m/z calcd for C$_{19}$H$_{24}$N$_3$O$_4$I 485.0812, found 485.0801.

Figure 11:
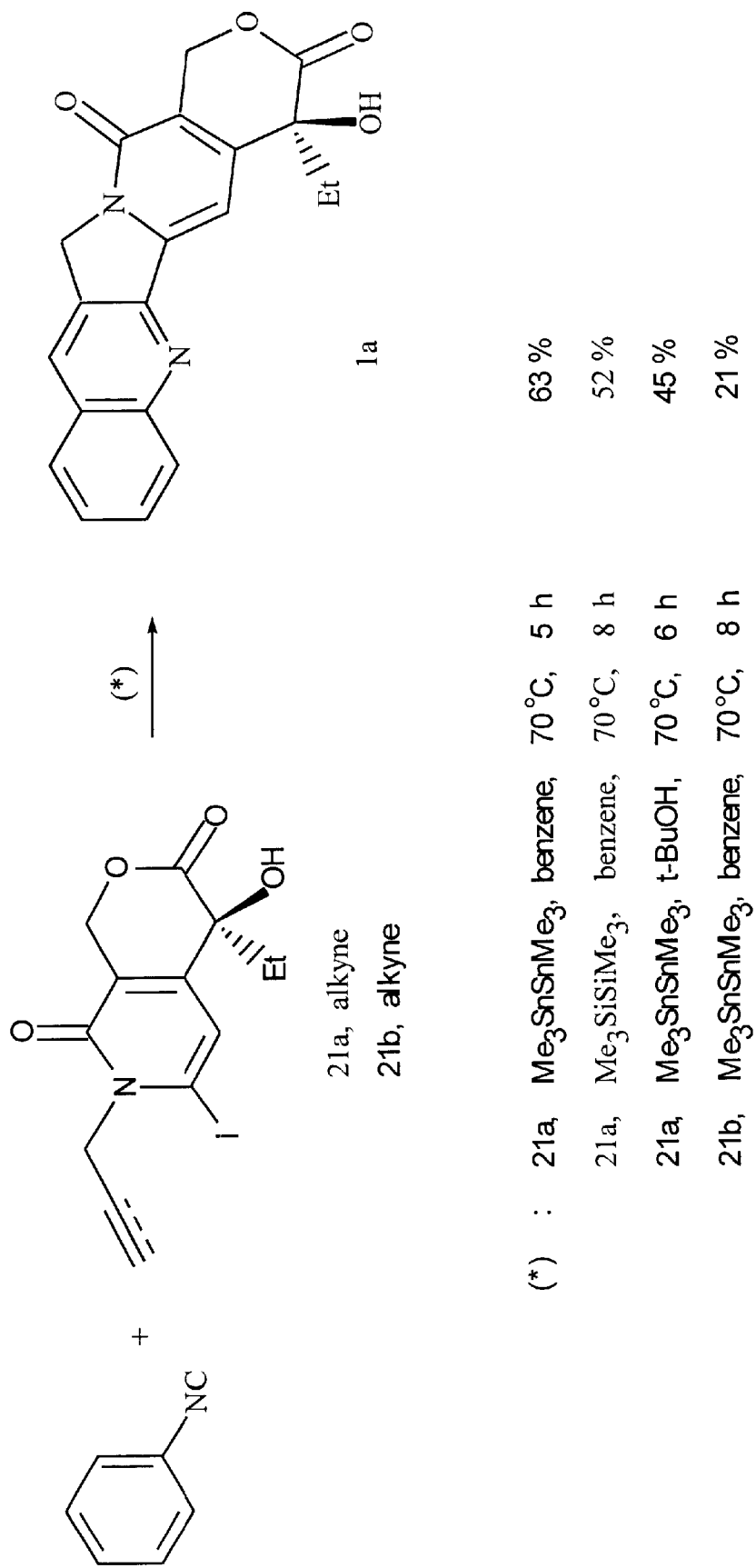
FIG. 11 provides an illustration of a novel synthesis of (20S)-camptothecin.
Figure 12:
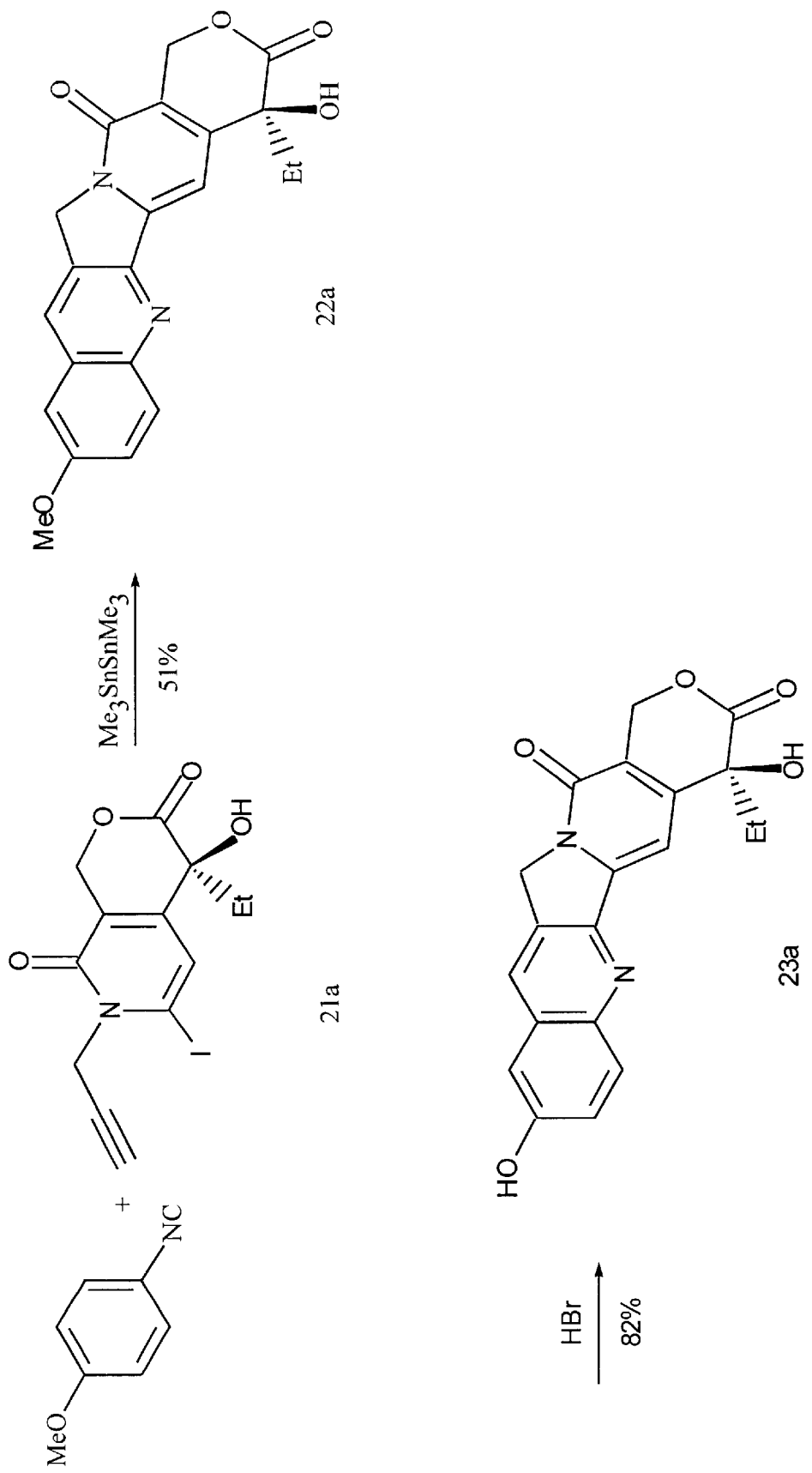
FIG. 12 provides an illustration of the synthesis of a known intermediate in the synthesis of (20S)-topotecan.
Figure 13:
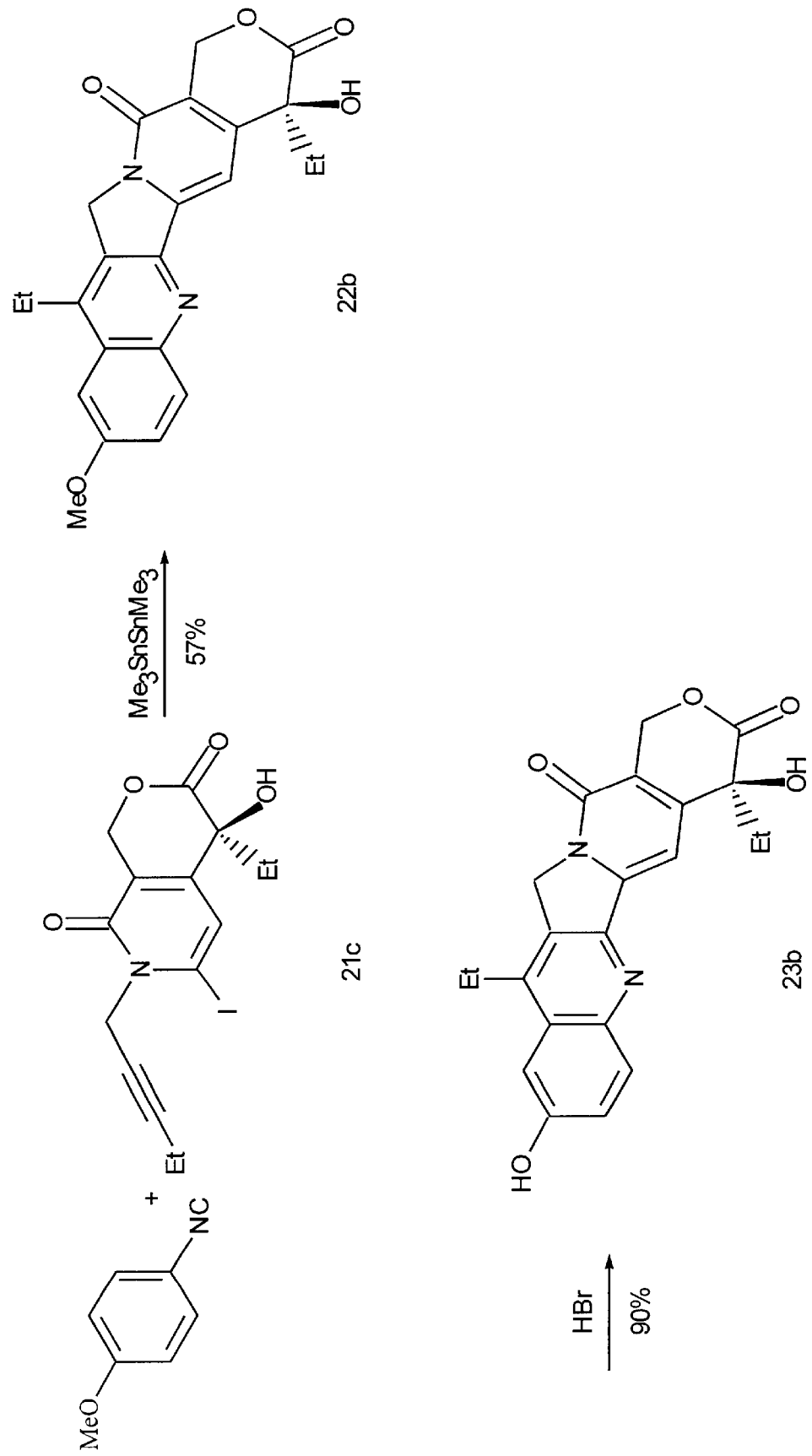
FIG. 13 provides an illustration of the synthesis of a known intermediate in the synthesis of (20S)-irinotecan.
Figure 14:
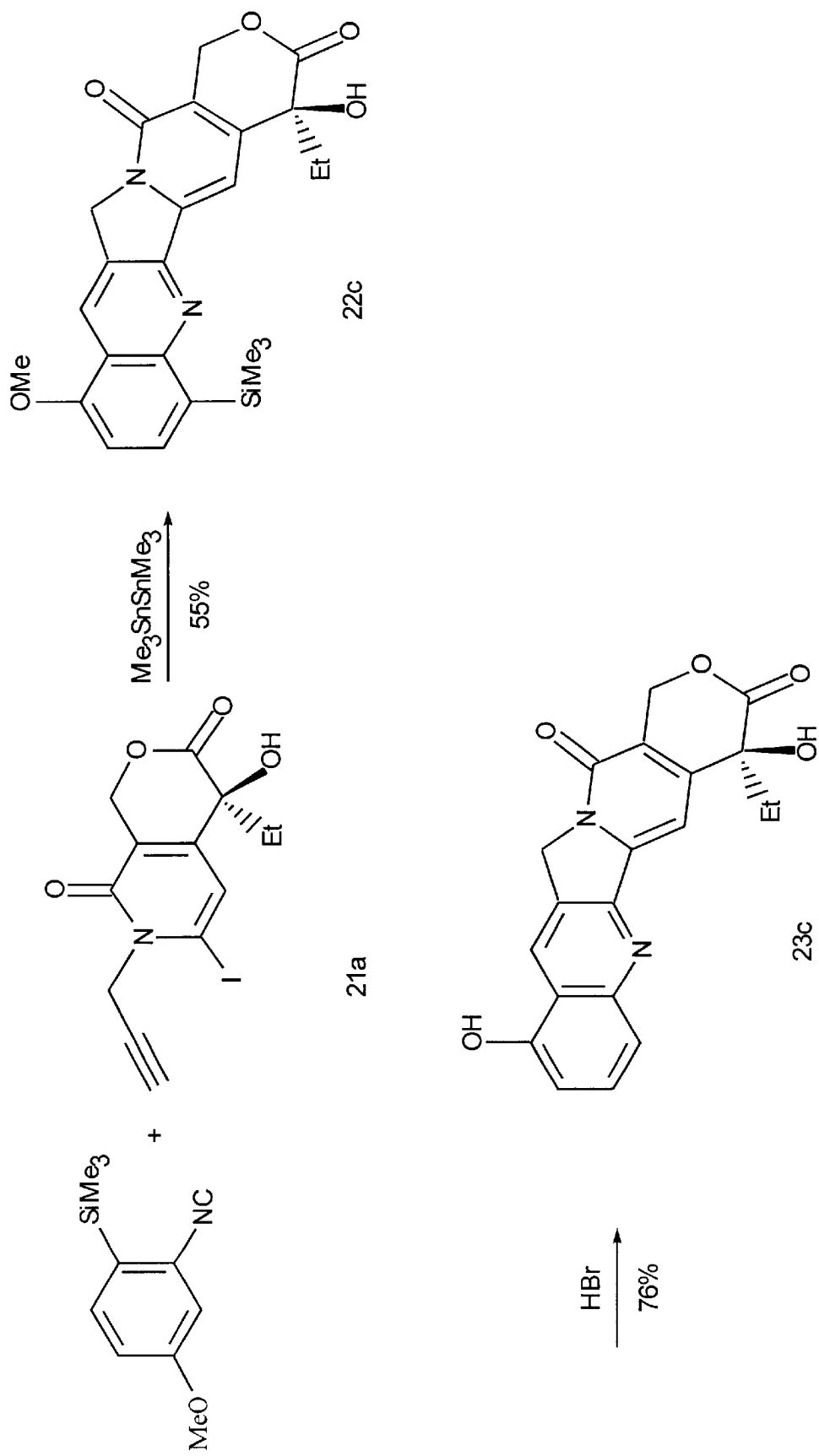
FIG. 14 provides an illustration of the preparation of (20S)-9-hydroxy-camptothecin derivatives.
Figure 15:
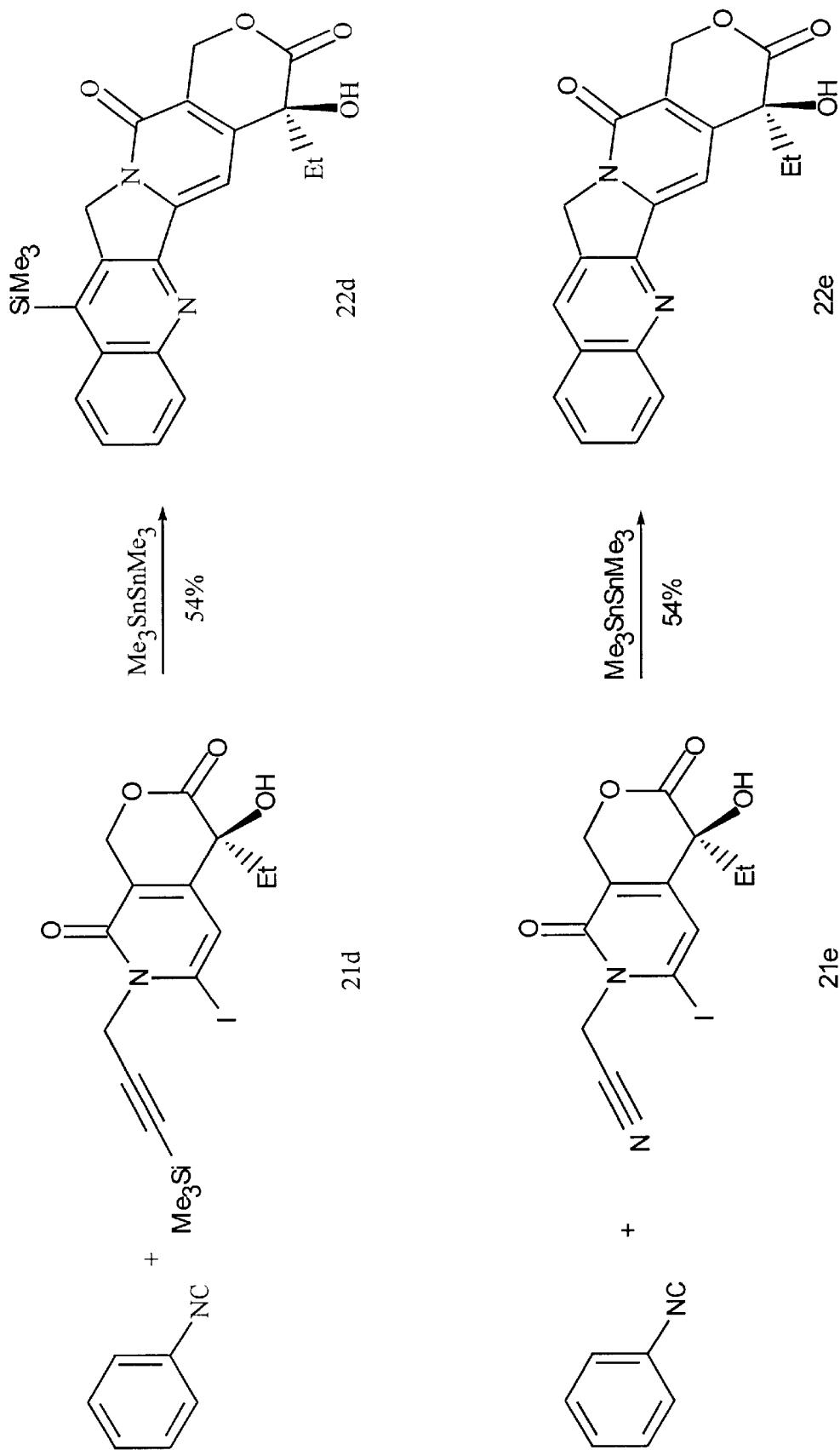
FIG. 15 provides an illustration of the preparation of a novel camptothecin derivative and (20S)-7-azacamptothecin.
Figure 16:
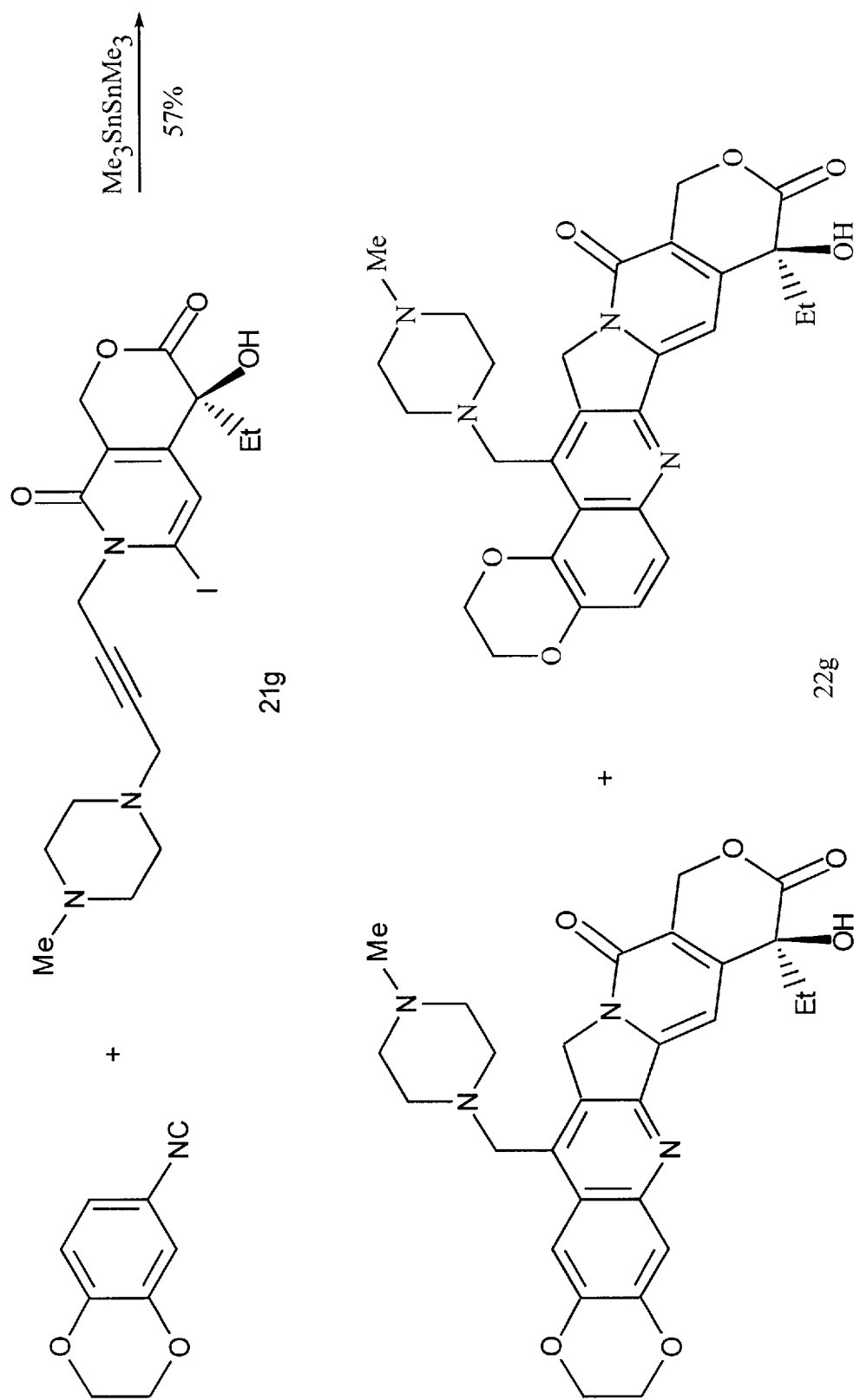
FIG. 16 provides an illustration of the preparation of known water-soluble derivatives of camptothecin.

The synthesis of (20S)-camptothecin is shown in FIG. 11. The procedure for the radical annulation/cyclization is preferably as described above for the synthesis of racemic camptothecin. Camptothecin can be made from both the allyl (21b) and propargyl (21a) precursors. The synthesis from the propargyl precursor (21a) is preferred.

(i) From the propargyl precursor: A solution of 21a (37.3 mg, 0.1 mmol), phenyl isonitrile (0.3 mmol) and hexamethylditin (51 mg, 0.15 mmol) in benzene (1.5 ml) under argon was irradiated at 70° C. with a 275W GE sunlamp for 5 h without stirring; every 0.5 h the vessel was tapped to allow the solid on the walls to drop to the bottom of the flask where it was protected from further irradiation. After cooling the solid was filtered, rinsed with Et$_2$O (2 mL), and then subjected to flash-chromatography (CHCl$_3$/CH$_3$CN/MeOH 90:5:5) to provide 21.8 mg (63%) of (20S)-camptothecin: [α]$^{20}_D$ +39.9 (c 0.2, CHCl$_3$/MeOH 4:1)[lit. +42.0 (c 0.51, CHCl$_3$/MeOH 4:1)]. Examples of other reaction conditions are shown in FIG. 11.

(ii) From the allyl precursor: In a similar manner 21b (40.1 mg, 0.107 mmol) provided 7.7 mg (21%) of (20S)-camptothecin.

A number of examples of preparation of camptothecin derivatives are shown in FIGS. 12 to 16. All products bear the 20(S) absolute configuration. Compounds 22a and 22b are known compounds Compounds 22a and 22b were converted to the known 10-hydroxyl camptothecin analogues 23a and 23b, respectively, by reaction with hydrobromic acid according to a procedure similar to that described by Danishefsky for a similar compound. See Danishefsky, S. J. et al., *J. Org. Chem.*, 58, 611 (1993). Topotecan has been obtained in one step from 23a. See Kingsbury, W. D. et al., *J. Med. Chem.*, 34, 98 (1991). Compound 23b has been converted in 1 step to irinotecan. See Sawada, S. et al., *Chem. Pharm. Bull.*, 39, 1446 (1991). Compound 22c is a novel compound and is an intermediate in the regioselective synthesis of the known compound 23c. Compound 23c is obtained from reacting 22c with hydrobromic acid. Compound 22d is novel. Compound 22e has been synthesized but only in its racemic form. See Terasawa, H. et al., *Heterocycles*, 38, 81 (1994). In the mixture 22g, the 10,11-ethylenedioxy isomer is a known compound, while the 9,10-ethylenedioxy isomer is novel. See Luzio, M. J. et al., *J. Med. Chem*, 38, 395 (1995).

EXAMPLE 9

The preparation of (20S)-10-hydroxy-camptothecin 23a proceeded in two steps. (i) (20S)-10-methoxycamptothecin 22a. The procedure described above for the synthesis of (20S)-camptothecin was followed, starting from 21a (43 mg, 0.12 mmol) and 4-methoxyphenyl isonitrile (40 mg, 0.30 mmol) to provide, after flash-chromatography (CHCl$_3$/MeOH 15:1), 22 mg (51%) of 22a as a white solid: [α]$^{20}_D$ +32.0 (c 0.74, CHCl$_3$/MeOH 4:1); $^1$H NMR (300 MHz, CDCl$_3$/CD$_3$OD 4:1) δ0.86 (t, J =7.3 Hz, 3 H), 1.78 (m, 2 H), 3.23 (s, 1 H), 3.82 (s, 3 H), 5.08 (s, 2 H), 5.13 (d, J=16.3 Hz, 1 H), 5.48 (d, J=16.3 Hz, 1 H), 7.03 (d, J=2.7 Hz, 1 H), 7.31 (dd, J=9.3 and 2.7 Hz, 1 H), 7.89 (d, J=9.3 Hz, 1 H), 8.16 (s, 1 H); $^{13}$C NMR (300 MHz, CDCl$_3$/CD$_3$OD 4:1) δ7.4, 31.1, 50.0, 55.4, 65.6, 72.7, 97.1, 105.3, 118.1, 123.8, 129.0, 129.6, 129.8, 130.2, 144.5, 146.1, 149.4, 151.1, 157.7, 158.9, 173.6; HRMS (EI) m/z calcd for C$_{21}$H$_{18}$N$_2$O$_5$ (M$^+$) 378.1216, found 378.1204.

(ii) (20S)-10-Hydroxycamptothecin 23a. A solution of 22a (2.7 mg, 0.0071 mmol) in 48% hydrobromic acid (0.5 mL) was heated to 110° C. for 3 days in a sealed tube and concentrated. Column chromatography (CH$_2$Cl$_2$/acetone/MeOH 30:10:2) provided 2.1 mg (82%) of 23a as a yellow solid: [α]$^{20}_D$ +35.3 (c 0.11, CH$_2$Cl$_2$/MeOH 4:1); $^1$H NMR (300 MHz, 5:1 CDCl$_3$/CD$_3$OD) δ0.92 (t, J=7.4 Hz, 3 H), 1.80 (m, 2 H), 5.10 (s, 2 H), 5.19 (d, J=16.3 Hz, 1 H), 5.56 (d, J=16.3 Hz, 1 H), 7.07 (d, J=2.7 Hz, 1 H), 7.33 (dd, J=9.30 and 2.67 Hz, 1 H), 7.91 (d, J=9.3 Hz, 1 H), 8.11 (s, 1 H); LRMS (EI) m/z 364 (M$^+$), 320, 305, 292, 264, 235.

EXAMPLE 10

The preparation of (20S)-7-ethyl-10-hydroxy-camptothecin 23b proceeded in 2 steps: (i) (20S)-7-ethyl-10-methoxycamptothecin 22b. The procedure described above for the synthesis of (20S)-camptothecin was followed, starting from 21c (40 mg, 0.10 mmol) and 4-methoxyphenyl isonitrile (27 mg, 0.20 mmol) to give, after flash-chromatography (CHCl$_3$/MeOH 20:1), 23 mg (57%) of 22b as a white solid: [α]$^{20}_D$ +19.1 (c 0.11, CHCl$_3$/MeOH 4:1); $^1$H NMR (300 MHz, CDCl$_3$/CD$_3$OD 10:1) δ0.91 (t, J=7.4 Hz, 3 H), 1.30 (t, J=7.62 Hz, 3 H), 1.81 (q, J=7.62 Hz, 2 H), 3.06 (q, J=7.41 Hz, 2 H), 3.88 (s, 3 H), 5.12 (s, 2 H), 5.18 (d, J=16.1 Hz, 1 H), 5.56 (d, J=16.1 Hz, 1 H), 7.21 (s, 1 H), 7.36 (d, J=9.3 Hz, 1 H), 7.53 (s, 1 H), 7.98 (d, J=9.3 Hz, 1 H); $^{13}$C NMR (300 MHz, CDCl$_3$/CD$_3$OD 10:1) 67.7, 13.4, 23.1, 31.4, 55.6, 66.0, 72.9, 98.0, 101,7, 118.1, 122.8, 127.3, 128.3, 131.5, 144.2, 145.1, 146.1, 149.3, 151.0, 157.8, 158.9, 173.8; HRMS (EI) m/z calcd for C$_{23}$H$_{22}$N$_2$O$_5$ (M$^+$) 406.1529, found 406.1550.

(ii) (20S)-7-Ethyl-10-hydroxycamptothecin 23b. Following the procedure described above for the synthesis of 23a, 22b (15 mg, 0.037 mmol) provided 13 mg (90%) of 23b as a yellow solid: [α]$^{20}_D$+29.3 (c 0.45, CH$_2$Cl$_2$/MeOH 4:1); $^1$H NMR (300 MHz, 5:1 CDCl$_3$/CD$_3$OD) δ0.83 (t, J=7.4 Hz, 3 H), 1.19 (t, J=7.62 Hz, 3 H), 1.75 (q, J=7.62 Hz, 2 H), 2.95 (q, J=7.41 Hz, 2 H), 5.08 (s, 2 H), 5.12 (d, J=16.1 Hz, 1 H), 5.47 (d, J=16.1 Hz, 1 H), 7.20 (s, 1 H), 7.22 (d, J=9.3 Hz, 1 H), 7.45 (s, 1 H), 7.85 (d, J=9.3 Hz, 1 H); HRMS (EI) m/z calcd for C$_{22}$H$_{20}$N$_2$O$_5$ (M$^+$) 392.1372, found 392.1338.

EXAMPLE 11

The preparation of (20S)-9-hydroxycamptothecin 23c proceeded in 2 steps: (i) (20S)-9-methoxy-12-trimethylsilylcamptothecin 22c. The procedure described above for the synthesis of (20S)-camptothecin was followed, starting from 21a (56.0 mg, 0.15 mmol) and 3-methoxy-6-trimethylsilylphenyl isonitrile (75.0 mg, 0.23 mmol) to afford, after flash-chromatographies (CHCl$_3$/MeOH 97:3 then CHCl$_3$/acetone 4:1), 37.1 mg (55%) of a slightly yellow solid: [α]$^{20}_D$+32.9 (c 1, CHCl$_3$); $^1$H NMR (300 MHz, CDCl$_3$) δ0.45 (s, 9 H), 1.03 (t, J=7.4 Hz, 3 H), 1.90 (m, 2 H), 3.91 (br s, 1 H), 4.01 (s, 3 H), 5.23 (br s, 2 H), 5.28 (d, J=16.3 Hz, 1 H), 5.72 (d, J=16.3 Hz, 1 H), 6.89 (d, J=7.7 Hz, 1 H), 7.47 (s, 1 H), 7.82 (d, J=7.7 Hz, 1 H), 8.75 (s, 1 H); $^{13}$C NMR (300 MHz, CDCl$_3$) δ0.0, 7.8, 31.4, 50.3, 55.8, 66.6, 72.7, 97.2, 105.1, 118.2, 120.5, 126.1, 127.0, 132.7, 137.0, 147.1, 150.3, 151.2, 153.6, 156.2, 157.7, 173.9;

HRMS (EI) m/z calcd for $C_{24}H_{26}N_2O_5Si$ (M⁺) 450.1611, found 450.1599; LRMS (EI) m/z 450 (M⁺, 34), 435 (100), 391 (33), 376 (30), 347 (16), 291 (21).

(ii). (20S)-9-Hydroxycamptothecin 23c. A mixture of 22c (17.2 mg, 0.038 mmol) and 48% aqueous hydrobromic acid (1 mL) was stirred in a sealed tube at 105° C. for 15 h. The final solution was concentrated to dryness then subjected to flash-chromatography (CHCl₃/MeOH 95:5 to 9:1) to provide 10.5 mg (76%) of a slightly yellow solid: $[\alpha]^{20}_D$ +32.0 (c 0.1, CHCl₃/CH₃OH 4:1); ¹H NMR (300 MHz, CDCl₃/CD₃OD 4:1) δ0.83 (t, J=7.4 Hz, 3 H), 1.74 (q, J=7.4 Hz, 1 H), 5.08 (br s, 2 H), 5.11 (d, J=16.4 Hz, 1 H), 5.47 (d, J=16.4 Hz, 1 H), 6.80 (d, J=8.5 Hz, 1 H), 7.40–7.50 (m, 2 H), 7.53 (s, 1 H), 8.68 (s, 1 H); HRMS (EI) m/z calcd for $C_{20}H_{16}N_2O_5$ (M⁺) 364.1059, found 364.1053; LRMS (EI) m/z 364 (M⁺, 94), 335 (44), 320 (100), 305 (59), 292 (64), 264 (96), 235 (75).

EXAMPLE 12

(20S)-7-Trimethylsilylcamptothecin 22d. The procedure described above for the synthesis of (20S)-camptothecin was followed, starting from 21d (36.6 mg, 0.082 mmol) to afford, after flash-chromatography (CHCl₃/MeOH 96:4), 18.8 mg (54%) of 22d as a slightly yellow solid: ¹H NMR (300 MHz, CDCl₃/CD₃OD 3:1) δ0.50 (s, 9 H), 0.83 (t, J=7.4 Hz, 3 H), 1.74 (m, 2 H), 3.72 (br s, 1 H), 5.12 (d, J=16.4 Hz, 1 H), 5.16 (br s, 2 H), 5.48 (d, J=16.4 Hz, 1 H), 7.49 (t, J=8.1 Hz, 1 H), 7.54 (s, 1 H), 7.62 (t, J=8.1 Hz, 1 H), 8.02 (d, J=8.1 Hz, 1 H), 8.07 (d, J=8.1 Hz, 1 H); ¹³C NMR (300 MHz, CDCl₃/CD₃OD 3:1) δ0.9, 7.2, 29.3, 31.0, 51.7, 65.5, 98.3, 118.4, 127.3, 128.0, 129.7, 130.0, 131.8, 134.3, 144.7, 145.6, 147.3, 151.1, 173.5; HRMS (EI) m/z calcd for $C_{23}H_{24}N_2O_4Si$ (M⁺) 420.1505, found 420.1501; LRMS (EI) m/z 420 (M⁺, 69), 391 (30), 376 (77), 361 (100), 347 (48), 320 (76), 291 (28).

Cytotoxicity and Topoisomerase I-mediated effect studies of compounds 22d and (20S)-camptothecin were performed at the Laboratory for Bioorganic Chemistry, Memorial Sloan-Kettering Institute Cancer Center, New York with the following results:

1. $IC_{50}$ (HL-60 human promyelocytic leukemic cells, μmol): 0.004 (22d); 0.004 (CPT).

2. $IC_{50}$ (833K human teratocarcinoma cells, μmol): 0.0044 (22d); 0.0055 (CPT).

3. Same potency for 22d and CPT in the inhibition of Topoisomerase I-mediated relaxation of supercoiled DNA, and in the induction of Topoisomerase I-mediated DNA cleavage.

EXAMPLE 13

(20S)-7-Azacamptothecin 22e. The procedure described above for the synthesis of (20S)-camptothecin was followed, starting from 21e (38.2 mg, 0.102 mmol) and phenyl isonitrile (0.30 mmol) to afford, after flash-chromatography (CHCl₃/acetone 4:1), 19.1 mg (54%) of a slightly yellow solid: $[\alpha]^{20}_D$+29.0 (c 0.1, CHCl₃/CH₃OH 4:1); ¹H NMR (300 MHz, CDCl₃) δ1.02 (t, J=7.3 Hz, 3 H), 1.88 (m, 2 H), 3.87 (br s, 1 H), 5.29 (d, =16.6 Hz, 1 H), 5.30 (br s, 2 H), 5.73 (d, J=16.6 Hz, 1 H), 7.69 (s, 1 H), 7.85–7.95 (m, 2 H), 8.18 (m, 1 H), 8.23 (m, 1 H); ¹³C NMR (300 MHz, CDCl₃) δ7.7, 31.6, 50.5, 66.3, 72.5, 99.4, 129.4, 129.9, 131.0, 131.5, 149.7; HRMS (EI) m/z calcd for $C_{19}H_{15}N_3O_4$ (M⁺) 349.1063, found 349.1052; LRMS (EI) m/z 349 (M⁺, 100), 320 (29), 305 (33), 290 (22), 276 (24), 249 (33), 220 (21).

EXAMPLE 14

10,11-Ethylenedioxy-7-(4-methylpyrazinomethyl)-camptothecin and 9,10-ethylenedioxy-7-(4-methylpyrazinomethyl)-camptothecin 22g (mixture 1:1 of the regioisomers). The procedure described above for the synthesis of (20S)-camptothecin was followed, starting from 21g (50 mg, 0.103 mmol) and 1,4-benzodioxan-6-isonitrile (33 mg, 0.205 mmol) to afford, after flash-chromatography (CH₂Cl₂/MeOH 4:1), 30 mg (57%) of the cyclized regioisomers: ¹H NMR (300 MHz, CDCl₃) δ7.22 (d, J=9.2 Hz, 1 H) and 7.50 (d, J=9.2 Hz, 1 H), from H-11 and H-12 of the 9,10-ethylenedioxy derivative; 7.05 (s, 1 H), 7.35 (s, 1 H), 7.42 (s, 1 H), and 7.43 (s, 1 H), from H-9 and H-12 of the 10,11-ethylenedioxy derivative, and the two H-14 of both isomers; 5.14 (s, 2 H) and 5.20 (s, 2 H) from the two H-5 of both isomers; 4.9–5.5 (m, 4 H) from 17-H (—CH₂O—) of both isomers; 4.27 (m, 4 H) and 4.34 (br s, 4 H) from ethylenedioxy (—OCH₂CH₂O—) of both isomers; 2.3–3.5 (m, 12 H) from the piperazine ring and the methylene position linked to the piperazine ring, from both isomers; 2.56 (s, 3 H) and 2.66 (s, 3 H) from N—CH₃ of both isomers; 1.7 (m, 4 H) from the methylene of Et, from both isomers; 0.8 (m, 5 H) from the methyl of Et, from both isomers.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A chemical compound having the formula

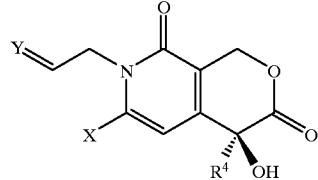

wherein X is selected from the group consisting of Br and I, Y is —CH₂ or —CHR³, R³ is hydrogen, a normal alkyl group, a branched alkyl group, an allyl group, a benzyl group, an alkynyl group, a propargyl group, an alkoxyl group, a halo group, a trialkylsilyl group, an amino group, an alkyl amino group, a dialkylamino group, an aminoalkyl group, a cyano group, and an acyl group and R⁴ is an alkyl group, an allyl group, a propargyl group or a benzyl group.

2. The chemical compound of claim 1 wherein R⁴ is an ethyl group —CH₂CH₃.

3. A chemical compound having the formula

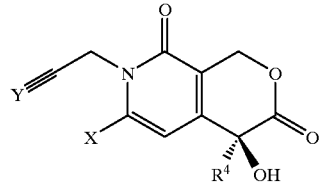

wherein X is I, Y is —N or —C—R³, R³ is hydrogen, a normal alkyl group, a branched alkyl group, an allyl group, a benzyl group, an alkynyl group, a propargyl group, an alkoxyl group, a halo group, a trialkylsilyl group, an amino group, an alkyl amino group, a dialkylamino group, an aminoalkyl group, a cyano group, and an acyl group and R⁴ is an alkyl group, an allyl group, a propargyl group nitrogen, —CH₂Cl, a 4-methylpyrazinomethyl group, or a benzyl group.

4. The chemical compound of claim 3 wherein $R^4$ is an ethyl group —$CH_2CH_3$.

5. The chemical compound of claim 3 wherein $R^3$ is selected from the group consisting of hydrogen, an ethyl group, a trimethilsylyl group, nitrogen, —$CH_2Cl$ and a 4-methylpyrazinomethyl group.

* * * * *